US010836829B2

(12) United States Patent
Mahr et al.

(10) Patent No.: US 10,836,829 B2
(45) Date of Patent: Nov. 17, 2020

(54) ANTI-WT1/HLA-SPECIFIC ANTIBODIES

(71) Applicants: immatics biotechnologies GmbH, Tuebingen (DE); MorphoSys AG, Martinsried/Planegg (DE)

(72) Inventors: Andrea Mahr, Tuebingen (DE); Toni Weinschenk, Aichwald (DE); Dominik Maurer, Reutlingen (DE); Claudia Wagner, Tuebingen (DE); Klaus Felix Hartlepp, Munich (DE); Alexandra Kraus, Munich (DE)

(73) Assignees: IMMATICS BIOTECHNOLOGIES GMBH, Tuebingen (DE); MORPHOSYS AG, Planegg (DE)

( * ) Notice: Subject to any disclaimer, the term of this patent is extended or adjusted under 35 U.S.C. 154(b) by 403 days.

(21) Appl. No.: 15/288,145

(22) Filed: Oct. 7, 2016

(65) Prior Publication Data
US 2017/0101473 A1 Apr. 13, 2017

Related U.S. Application Data

(60) Provisional application No. 62/239,438, filed on Oct. 9, 2015.

(30) Foreign Application Priority Data

Oct. 9, 2015 (GB) .................................. 1517913.8
Oct. 14, 2015 (EP) .................................... 15189753

(51) Int. Cl.
| | |
|---|---|
| *A61K 39/00* | (2006.01) |
| *C07K 16/28* | (2006.01) |
| *C07K 16/18* | (2006.01) |
| *G01N 33/53* | (2006.01) |
| *C07K 14/47* | (2006.01) |
| *G01N 33/68* | (2006.01) |
| *C07K 14/74* | (2006.01) |

(52) U.S. Cl.
CPC ...... *C07K 16/2833* (2013.01); *C07K 14/4748* (2013.01); *C07K 16/18* (2013.01); *G01N 33/53* (2013.01); *G01N 33/6854* (2013.01); *A61K 2039/505* (2013.01); *C07K 2317/21* (2013.01); *C07K 2317/32* (2013.01); *C07K 2317/33* (2013.01); *C07K 2317/34* (2013.01); *C07K 2317/55* (2013.01); *C07K 2317/565* (2013.01); *C07K 2317/732* (2013.01); *G01N 2500/04* (2013.01)

(58) Field of Classification Search
None
See application file for complete search history.

(56) References Cited

U.S. PATENT DOCUMENTS

2014/0271644 A1   9/2014   Scheinberg et al.

FOREIGN PATENT DOCUMENTS

| WO | 2012135854 A2 | 10/2012 |
| WO | 2015070061 A1 | 5/2015 |

OTHER PUBLICATIONS

Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
De Pascalis et al (The Journal of Immunology (2002) 169: 3076-3084) (Year: 2002).*
Casset et al (BBRC, 2003, 307: 198-205) (Year: 2003).*
Holm et al (Molecular Immunol. 2007, 44, 1075-1084) (Year: 2007).*
Veomett et al (Clinical Cancer Res. 20(15): 4036-4046, published online May 21, 2014) (Year: 2014).*
Great Britain Search Report dated Jul. 20, 2016 issued in counterpart GB Application No. 1517913.8.
Zhao et al., "Affinity maturation of T-cell receptor-like antibodies for Wilms tumor 1 peptide greatly enhances therapeutic potential" Leukemia. (2015) vol. 29: 2238-2247.
Linette et al., "Cardiovascular toxicity and titin cross-reactivity of affinity-enhanced T cells in myeloma and melanoma" Blood. (Aug. 8, 2013) vol. 122, No. 6: 863-872.
Lundegaard et al., "NetMHC-3.0: accurate web accessible predictions of human, mouse and monkey MHC clas I affinities for peptides of length 8-11" Nucleic Acids Research. (2008) vol. 36: W510-W512.

* cited by examiner

*Primary Examiner* — Michael Szperka
*Assistant Examiner* — Marianne DiBrino
(74) *Attorney, Agent, or Firm* — McBee Moore & Vanik IP, LLC

(57) ABSTRACT

The present invention relates to antibodies or fragments thereof binding to human WT1/HLA. In particular, the present invention relates to antibodies or fragments thereof that have combined improved and/or beneficial properties, and are therefore suited for clinical development.

13 Claims, 6 Drawing Sheets

Specification includes a Sequence Listing.

SEQUENCE LISTING

```
<160> NUMBER OF SEQ ID NOS: 64

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 449
<212> TYPE: PRT
<213> ORGANISM: Homo sapiens

<400> SEQUENCE: 2

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Pro Ala Pro Pro Pro Pro Pro
        50                  55                  60

Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
```

```
                145                 150                 155                 160
Gly His Thr Pro Ser His His Ala Ala Gln Phe Pro Asn His Ser Phe
                    165                 170                 175
Lys His Glu Asp Pro Met Gly Gln Gln Gly Ser Leu Gly Glu Gln Gln
                180                 185                 190
Tyr Ser Val Pro Pro Val Tyr Gly Cys His Thr Pro Thr Asp Ser
            195                 200                 205
Cys Thr Gly Ser Gln Ala Leu Leu Leu Arg Thr Pro Tyr Ser Ser Asp
210                 215                 220
Asn Leu Tyr Gln Met Thr Ser Gln Leu Glu Cys Met Thr Trp Asn Gln
225                 230                 235                 240
Met Asn Leu Gly Ala Thr Leu Lys Gly Val Ala Ala Gly Ser Ser Ser
                245                 250                 255
Ser Val Lys Trp Thr Glu Gly Gln Ser Asn His Ser Thr Gly Tyr Glu
                260                 265                 270
Ser Asp Asn His Thr Thr Pro Ile Leu Cys Gly Ala Gln Tyr Arg Ile
                275                 280                 285
His Thr His Gly Val Phe Arg Gly Ile Gln Asp Val Arg Arg Val Pro
    290                 295                 300
Gly Val Ala Pro Thr Leu Val Arg Ser Ala Ser Glu Thr Ser Glu Lys
305                 310                 315                 320
Arg Pro Phe Met Cys Ala Tyr Pro Gly Cys Asn Lys Arg Tyr Phe Lys
                325                 330                 335
Leu Ser His Leu Gln Met His Ser Arg Lys His Thr Gly Glu Lys Pro
                340                 345                 350
Tyr Gln Cys Asp Phe Lys Asp Cys Glu Arg Arg Phe Ser Arg Ser Asp
                355                 360                 365
Gln Leu Lys Arg His Gln Arg Arg His Thr Gly Val Lys Pro Phe Gln
                370                 375                 380
Cys Lys Thr Cys Gln Arg Lys Phe Ser Arg Ser Asp His Leu Lys Thr
385                 390                 395                 400
His Thr Arg Thr His Thr Gly Lys Thr Ser Glu Lys Pro Phe Ser Cys
                    405                 410                 415
Arg Trp Pro Ser Cys Gln Lys Lys Phe Ala Arg Ser Asp Glu Leu Val
                420                 425                 430
Arg His His Asn Met His Gln Arg Asn Met Thr Lys Leu Gln Leu Ala
                435                 440                 445
Leu

<210> SEQ ID NO 3
<211> LENGTH: 357
<212> TYPE: DNA
<213> ORGANISM: Homo sapiens

<400> SEQUENCE: 3
caggtgcagc tggtggaaag cggcggtggc ctggtgaaac aggcggtag cctgcgcctg      60 agctgcgccg ccagcggctt tacctttagc gatcattaca ttagctggat tcgccaggcc    120
ccaggcaaag gcctggaatg ggttagctat attagcagca gtggcagcac cacctattac    180
gccgagagcg tgaaaggccg ctttaccatt agccgcgata acgccaaaaa cagcctgtat    240
ctgcaaatga acagcctgcg ggccgaagat accgccgtgt attattgcgc gcgtacttac    300
gcatatcgtt acgattttga tctgtggggc caggcaccc tggttactgt ctcgagc       357
```

<210> SEQ ID NO 4
<211> LENGTH: 339
<212> TYPE: DNA
<213> ORGANISM: Homo sapiens

<400> SEQUENCE: 4

```
cagagcgtgc tgacccagcc accaagcgtg agcggtgcac caggtcagcg cgtgaccatt    60
agctgcaccg gcagcagcag caacattggc gcaggctatg atgtgcattg gtatcagcag   120
ctgccaggca ccgcaccgaa actgctgatt tatggcaaca gcaatcgccc aagcggtgtg   180
ccggatcgct ttagcggcag caaaagcggc accagcgcca gcctggcgat taccggtctg   240
caagccgaag acgaagccga ttattactgc cagacttggg ttcattctta ctctactccg   300
gtgtttggcg gcggtaccaa gctgaccgtg ctgggccag                          339
```

<210> SEQ ID NO 5
<211> LENGTH: 119
<212> TYPE: PRT
<213> ORGANISM: Homo sapiens

<400> SEQUENCE: 5

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Ile Ser Trp Ile Arg Gln Ala Pro Gly Lys Gly Leu Glu Trp Val
        35                  40                  45

Ser Tyr Ile Ser Ser Ser Gly Ser Thr Thr Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Tyr Ala Tyr Arg Tyr Asp Phe Asp Leu Trp Gly Gln Gly
            100                 105                 110

Thr Leu Val Thr Val Ser Ser
        115
```

<210> SEQ ID NO 6
<211> LENGTH: 113
<212> TYPE: PRT
<213> ORGANISM: Homo sapiens

<400> SEQUENCE: 6

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Thr Trp Val His Ser
                85                  90                  95

Tyr Ser Thr Pro Val Phe Gly Gly Gly Thr Lys Leu Thr Val Leu Gly
            100                 105                 110
```

Gln

<210> SEQ ID NO 7
<211> LENGTH: 5
<212> TYPE: PRT
<213> ORGANISM: Homo sapiens

<400> SEQUENCE: 7

Asp His Tyr Ile Ser
1               5

<210> SEQ ID NO 8
<211> LENGTH: 17
<212> TYPE: PRT
<213> ORGANISM: Homo sapiens

<400> SEQUENCE: 8

Tyr Ile Ser Ser Ser Gly Ser Thr Thr Tyr Tyr Ala Glu Ser Val Lys
1               5                   10                  15

Gly

<210> SEQ ID NO 9
<211> LENGTH: 10
<212> TYPE: PRT
<213> ORGANISM: Homo sapiens

<400> SEQUENCE: 9

Thr Tyr Ala Tyr Arg Tyr Asp Phe Asp Leu
1               5                   10

<210> SEQ ID NO 10
<211> LENGTH: 14
<212> TYPE: PRT
<213> ORGANISM: Homo sapiens

<400> SEQUENCE: 10

Thr Gly Ser Ser Ser Asn Ile Gly Ala Gly Tyr Asp Val His
1               5                   10

<210> SEQ ID NO 11
<211> LENGTH: 7
<212> TYPE: PRT
<213> ORGANISM: Homo sapiens

<400> SEQUENCE: 11

Gly Asn Ser Asn Arg Pro Ser
1               5

<210> SEQ ID NO 12
<211> LENGTH: 11
<212> TYPE: PRT
<213> ORGANISM: Homo sapiens

<400> SEQUENCE: 12

Gln Thr Trp Val His Ser Tyr Ser Thr Pro Val
1               5                   10

<210> SEQ ID NO 13
<211> LENGTH: 360
<212> TYPE: DNA
<213> ORGANISM: Homo sapiens

<400> SEQUENCE: 13

```
gaagtgcagc tggtggaaag cggcggtggc ctggtgaaac caggcggtag cctgcgcctg    60
agctgcgccg ccagcggctt tacctttagc agctatagca tgaactgggt tcgccaggcc   120
ccaggcaaag gcctggaatg ggttagcagc atcagcagca gtagcagcta tctattac    180 gccgatagcg tgaaaggccg ctttaccatt agcgcgata cgccaaaaaa cagcctgtat    240
ctgcaaatga acagcctgcg ggccgaagat accgccgtgt attattgcgc gcgaactgag    300
agcgtttggc acctgggttt cgatatttgg ggccagggca ccctggttac tgtctcgagc    360
```

<210> SEQ ID NO 14
<211> LENGTH: 327
<212> TYPE: DNA
<213> ORGANISM: Homo sapiens

<400> SEQUENCE: 14

```
gatattcaga tgacccagag cccgagcagc gttagcgcca gcgtgggcga tcgcgtgacc    60
attacctgcc gcgccagtca gggcattagc agctggctgg cctggtatca gcagaaaccg   120
ggcaaagccc cgaaactgct gatctatgcc gccagcagcc tgcaaagcgg cgtgccaagt   180
cgctttagcg gcagcggtag cggcaccgat ttcaccctga ccattagcag tctgcaaccg   240
gaagactttg ccacctatta ttgccagcag aaccataaat acccgatcac cttcggccag   300
ggtaccaaag tggaaatcaa gcggacc                                       327
```

<210> SEQ ID NO 15
<211> LENGTH: 120
<212> TYPE: PRT
<213> ORGANISM: Homo sapiens

<400> SEQUENCE: 15

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Glu Ser Val Trp His Leu Gly Phe Asp Ile Trp Gly Gln
            100                 105                 110

Gly Thr Leu Val Thr Val Ser Ser
        115                 120
```

<210> SEQ ID NO 16
<211> LENGTH: 109
<212> TYPE: PRT
<213> ORGANISM: Homo sapiens

<400> SEQUENCE: 16

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
```

```
                35                  40                  45
Tyr Ala Ala Ser Ser Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Asn His Lys Tyr Pro Ile
                85                  90                  95
Thr Phe Gly Gln Gly Thr Lys Val Glu Ile Lys Arg Thr
            100                 105
```

<210> SEQ ID NO 17
<211> LENGTH: 5
<212> TYPE: PRT
<213> ORGANISM: Homo sapiens

<400> SEQUENCE: 17

```
Ser Tyr Ser Met Asn
1               5
```

<210> SEQ ID NO 18
<211> LENGTH: 17
<212> TYPE: PRT
<213> ORGANISM: Homo sapiens

<400> SEQUENCE: 18

```
Ser Ile Ser Ser Ser Ser Ser Tyr Ile Tyr Tyr Ala Asp Ser Val Lys
1               5                   10                  15
Gly
```

<210> SEQ ID NO 19
<211> LENGTH: 11
<212> TYPE: PRT
<213> ORGANISM: Homo sapiens

<400> SEQUENCE: 19

```
Thr Glu Ser Val Trp His Leu Gly Phe Asp Ile
1               5                   10
```

<210> SEQ ID NO 20
<211> LENGTH: 11
<212> TYPE: PRT
<213> ORGANISM: Homo sapiens

<400> SEQUENCE: 20

```
Arg Ala Ser Gln Gly Ile Ser Ser Trp Leu Ala
1               5                   10
```

<210> SEQ ID NO 21
<211> LENGTH: 7
<212> TYPE: PRT
<213> ORGANISM: Homo sapiens

<400> SEQUENCE: 21

```
Ala Ala Ser Ser Leu Gln Ser
1               5
```

<210> SEQ ID NO 22
<211> LENGTH: 9
<212> TYPE: PRT
<213> ORGANISM: Homo sapiens

<400> SEQUENCE: 22

Gln Gln Asn His Lys Tyr Pro Ile Thr
1               5

<210> SEQ ID NO 23
<211> LENGTH: 360
<212> TYPE: DNA
<213> ORGANISM: Homo sapiens

<400> SEQUENCE: 23
caggtgcagc tggtggaaag cggcggtggc ctggtgaaac caggcggtag cctgcgcctg     60
agctgcgccg ccagcggctt tacctttagc gattactaca tgagctggat tcgccaggcc    120
ccaggcaaag cctggaatg ggttagctat attagcagca gtggcagcac catctattac    180
gccgatagcg tgaaaggccg ctttaccatt agccgcgata cgccaaaaa cagcctgtat    240 ctgcaaatga acagcctgcg ggccgaagat accgccgtgt attattgcgc gcgtgacgga    300
ctgcgttact ctatggatt tgattactgg ggccagggca ccctggttac tgtctcgagc    360

<210> SEQ ID NO 24
<211> LENGTH: 339
<212> TYPE: DNA
<213> ORGANISM: Homo sapiens

<400> SEQUENCE: 24
cagagcgtgc tgacccagcc gccgagcgtt agcgccgcac caggccagaa agtgaccatt     60
agctgtagcg gcagcagcag caacatcggc aacaactacg ttagctggta tcagcagctg    120
ccgggcaccg ccccgaaact gctgatctat gataacaaca aacgcccgag cggcatcccg    180
gatcgcttta gcggtagcaa aagcggcacc agcgccaccc tgggcattac cggcctgcaa    240
accgaagacg aagccgatta ttactgccag gcttgggttc attactctct ggttcattgg    300
gtgtttggcg gcggtaccaa gctgaccgtg ctgggccag                           339

<210> SEQ ID NO 25
<211> LENGTH: 120
<212> TYPE: PRT
<213> ORGANISM: Homo sapiens

<400> SEQUENCE: 25

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Arg Tyr Phe Tyr Gly Phe Asp Tyr Trp Gly Gln
            100                 105                 110

Gly Thr Leu Val Thr Val Ser Ser
        115                 120

<210> SEQ ID NO 26
<211> LENGTH: 113
<212> TYPE: PRT

<213> ORGANISM: Homo sapiens

<400> SEQUENCE: 26

Gln Ser Val Leu Thr Gln Pro Pro Ser Val Ser Ala Ala Pro Gly Gln
1               5                   10                  15
Lys Val Thr Ile Ser Cys Ser Gly Ser Ser Ser Asn Ile Gly Asn Asn
            20                  25                  30
Tyr Val Ser Trp Tyr Gln Gln Leu Pro Gly Thr Ala Pro Lys Leu Leu
        35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Glu Asp Glu Ala Asp Tyr Tyr Cys Gln Ala Trp Val His Tyr Ser
                85                  90                  95
Leu Val His Trp Val Phe Gly Gly Gly Thr Lys Leu Thr Val Leu Gly
            100                 105                 110
Gln

<210> SEQ ID NO 27
<211> LENGTH: 5
<212> TYPE: PRT
<213> ORGANISM: Homo sapiens

<400> SEQUENCE: 27

Asp Tyr Tyr Met Ser
1               5

<210> SEQ ID NO 28
<211> LENGTH: 17
<212> TYPE: PRT
<213> ORGANISM: Homo sapiens

<400> SEQUENCE: 28

Tyr Ile Ser Ser Ser Gly Ser Thr Ile Tyr Tyr Ala Asp Ser Val Lys
1               5                   10                  15
Gly

<210> SEQ ID NO 29
<211> LENGTH: 11
<212> TYPE: PRT
<213> ORGANISM: Homo sapiens

<400> SEQUENCE: 29

Asp Gly Leu Arg Tyr Phe Tyr Gly Phe Asp Tyr
1               5                   10

<210> SEQ ID NO 30
<211> LENGTH: 13
<212> TYPE: PRT
<213> ORGANISM: Homo sapiens

<400> SEQUENCE: 30

Ser Gly Ser Ser Ser Asn Ile Gly Asn Asn Tyr Val Ser
1               5                   10

<210> SEQ ID NO 31
<211> LENGTH: 7
<212> TYPE: PRT
<213> ORGANISM: Homo sapiens

<400> SEQUENCE: 31

Asp Asn Asn Lys Arg Pro Ser
1               5

<210> SEQ ID NO 32
<211> LENGTH: 12
<212> TYPE: PRT
<213> ORGANISM: Homo sapiens

<400> SEQUENCE: 32

Gln Ala Trp Val His Tyr Ser Leu Val His Trp Val
1               5                   10

<210> SEQ ID NO 33
<211> LENGTH: 366
<212> TYPE: DNA
<213> ORGANISM: Homo sapiens

<400> SEQUENCE: 33
caggtgcagc tggtgcagag cggtgccgaa gtgaaaaaac caggcgccag cgtgaaagtt     60
agctgcaaag ccagcggcta taccttcacc agctactata tgcattgggt tcgccaggcc    120
ccaggccagg gtctggaatg gatgggcatt attaacccga gcggcggcag caccagctat    180
gcacagaaat ttcagggccg cgtgaccatg acccgcgata ccagcaccag caccgtgtat    240
atggaactga gcagcctgcg cagcgaagat accgccgtgt attattgcgc gcgtgagggt    300
tacactcctg gtggtagcta cactttcgac atctggggtc agggcaccct ggttactgtc    360
tcgagc                                                               366

<210> SEQ ID NO 34
<211> LENGTH: 339
<212> TYPE: DNA
<213> ORGANISM: Homo sapiens

<400> SEQUENCE: 34
cagagcgtgc tgacccagcc gccgagcgtt agcgccgcac caggccagaa agtgaccatt     60
agctgtagcg gcagcagcag caacatcggc aacaactacg ttagctggta tcagcagctg    120
ccgggcaccg ccccgaaact gctgatctat gataacaaca acgcccgag cggcatcccg     180 gatcgcttta gcggtagcaa aagcggcacc agcgccaccc tgggcattac cggcctgcaa    240
accgaagacg aagccgatta ttactgcggt tcttgggacg tttcgtttc ttcttactct     300 gtgtttggcg gcggtaccaa gctgaccgtg ctgggccag                            339

<210> SEQ ID NO 35
<211> LENGTH: 122
<212> TYPE: PRT
<213> ORGANISM: Homo sapiens

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr

```
                65                  70                  75                  80
Met Glu Leu Ser Ser Leu Arg Ser Glu Asp Thr Ala Val Tyr Tyr Cys
                    85                  90                  95
Ala Arg Glu Gly Tyr Thr Pro Gly Gly Ser Tyr Thr Phe Asp Ile Trp
                100                 105                 110
Gly Gln Gly Thr Leu Val Thr Val Ser Ser
        115                 120
```

<210> SEQ ID NO 36
<211> LENGTH: 113
<212> TYPE: PRT
<213> ORGANISM: Homo sapiens

<400> SEQUENCE: 36

```
Gln Ser Val Leu Thr Gln Pro Pro Ser Val Ser Ala Ala Pro Gly Gln
1               5                   10                  15
Lys Val Thr Ile Ser Cys Ser Gly Ser Ser Ser Asn Ile Gly Asn Asn
                20                  25                  30
Tyr Val Ser Trp Tyr Gln Gln Leu Pro Gly Thr Ala Pro Lys Leu Leu
            35                  40                  45
Ile Tyr Asp Asn Asn Lys Arg Pro Ser Gly Ile Pro Asp Arg Phe Ser
    50                  55                  60
Gly Ser Lys Ser Gly Thr Ser Ala Thr Leu Gly Ile Thr Gly Leu Gln
65                  70                  75                  80
Thr Glu Asp Glu Ala Asp Tyr Tyr Cys Gly Ser Trp Asp Gly Phe Val
                85                  90                  95
Ser Ser Tyr Ser Val Phe Gly Gly Gly Thr Lys Leu Thr Val Leu Gly
                100                 105                 110
Gln
```

<210> SEQ ID NO 37
<211> LENGTH: 5
<212> TYPE: PRT
<213> ORGANISM: Homo sapiens

<400> SEQUENCE: 37

```
Ser Tyr Tyr Met His
1               5
```

<210> SEQ ID NO 38
<211> LENGTH: 17
<212> TYPE: PRT
<213> ORGANISM: Homo sapiens

<400> SEQUENCE: 38

```
Ile Ile Asn Pro Ser Gly Gly Ser Thr Ser Tyr Ala Gln Lys Phe Gln
1               5                   10                  15
Gly
```

<210> SEQ ID NO 39
<211> LENGTH: 13
<212> TYPE: PRT
<213> ORGANISM: Homo sapiens

<400> SEQUENCE: 39

```
Glu Gly Tyr Thr Pro Gly Gly Ser Tyr Thr Phe Asp Ile
1               5                   10
```

<210> SEQ ID NO 40

-continued

<211> LENGTH: 13
<212> TYPE: PRT
<213> ORGANISM: Homo sapiens

<400> SEQUENCE: 40

Ser Gly Ser Ser Ser Asn Ile Gly Asn Asn Tyr Val Ser
1               5                   10

<210> SEQ ID NO 41
<211> LENGTH: 7
<212> TYPE: PRT
<213> ORGANISM: Homo sapiens

<400> SEQUENCE: 41

Asp Asn Asn Lys Arg Pro Ser
1               5

<210> SEQ ID NO 42
<211> LENGTH: 12
<212> TYPE: PRT
<213> ORGANISM: Homo sapiens

<400> SEQUENCE: 42

Gly Ser Trp Asp Gly Phe Val Ser Ser Tyr Ser Val
1               5                   10

<210> SEQ ID NO 43
<211> LENGTH: 354
<212> TYPE: DNA
<213> ORGANISM: Homo sapiens

<400> SEQUENCE: 43
gaagtgcagc tggtgcagag cggtgccgaa gtgaaaaaac cgggcgaaag cctgaaaatc        60
agctgcaaag gcagcggcta tagctttacc agctattgga ttagctgggt tcgccagatg       120
ccgggcaaag gcctggaatg gatgggcatt atctatccgg gcaccagcta tacccgctat       180
agcccgagct ttcagggcca ggttacaatt agcgccgaca aaagcatcag caccgcctat       240
ctgcaatgga gcagcctgaa agccagcgat accgccatgt attattgcgc gcgaggatac       300
cacctgcctt actttgatta ctggggccag ggcacccctgg ttactgtctc gagc            354

<210> SEQ ID NO 44
<211> LENGTH: 336
<212> TYPE: DNA
<213> ORGANISM: Homo sapiens

<400> SEQUENCE: 44
cagagcgtgc tgacccagcc accaagcgtg agcggtgcac caggtcagcg cgtgaccatt        60
agctgcaccg gcagcagcag caacattggc gcaggctatg atgtgcattg gtatcagcag       120
ctgccaggca ccgcaccgaa actgctgatt tatggcaaca gcaatcgccc aagcggtgtg       180
ccggatcgct ttagcggcag caaaagcggc accagcgcca gcctggcgat taccggtctg       240
caagccgaag acgaagccga ttattactgc caggcttacg cttctccgac tcgtgttgtg       300
tttggcggcg gtaccaagct gaccgtgctg ggccag                                  336

<210> SEQ ID NO 45
<211> LENGTH: 118
<212> TYPE: PRT
<213> ORGANISM: Homo sapiens

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
            35                  40                  45

Gly Ile Ile Tyr Pro Gly Thr Ser Tyr Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr His Leu Pro Tyr Phe Asp Tyr Trp Gly Gln Gly Thr
                100                 105                 110

Leu Val Thr Val Ser Ser
            115

<210> SEQ ID NO 46
<211> LENGTH: 112
<212> TYPE: PRT
<213> ORGANISM: Homo sapiens

<400> SEQUENCE: 46

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ala Tyr Ala Ser Pro
                85                  90                  95

Thr Arg Val Val Phe Gly Gly Gly Thr Lys Leu Thr Val Leu Gly Gln
                100                 105                 110

<210> SEQ ID NO 47
<211> LENGTH: 5
<212> TYPE: PRT
<213> ORGANISM: Homo sapiens

<400> SEQUENCE: 47

Ser Tyr Trp Ile Ser
1               5

<210> SEQ ID NO 48
<211> LENGTH: 17
<212> TYPE: PRT
<213> ORGANISM: Homo sapiens

<400> SEQUENCE: 48

Ile Ile Tyr Pro Gly Thr Ser Tyr Thr Arg Tyr Ser Pro Ser Phe Gln
1               5                   10                  15

Gly

<210> SEQ ID NO 49

-continued

```
<211> LENGTH: 9
<212> TYPE: PRT
<213> ORGANISM: Homo sapiens

<400> SEQUENCE: 49

Gly Tyr His Leu Pro Tyr Phe Asp Tyr
1               5

<210> SEQ ID NO 50
<211> LENGTH: 14
<212> TYPE: PRT
<213> ORGANISM: Homo sapiens

<400> SEQUENCE: 50

Thr Gly Ser Ser Ser Asn Ile Gly Ala Gly Tyr Asp Val His
1               5                   10

<210> SEQ ID NO 51
<211> LENGTH: 7
<212> TYPE: PRT
<213> ORGANISM: Homo sapiens

<400> SEQUENCE: 51

Gly Asn Ser Asn Arg Pro Ser
1               5

<210> SEQ ID NO 52
<211> LENGTH: 10
<212> TYPE: PRT
<213> ORGANISM: Homo sapiens

<400> SEQUENCE: 52

Gln Ala Tyr Ala Ser Pro Thr Arg Val Val
1               5                   10

<210> SEQ ID NO 53
<211> LENGTH: 366
<212> TYPE: DNA
<213> ORGANISM: Homo sapiens

<400> SEQUENCE: 53
gaagtgcagc tggtggaaag cggcggtggc ctggtgaaac caggcggtag cctgcgcctg      60
agctgcgccg ccagcggctt tacctttagc aactattgga ttagctgggt cgccaggcc     120 ccaggcaaag gcctggaatg ggttggccgc atcaaaagca aaacctatgg cggcaccacc     180
gattatgccg agccagtgaa aggccgcttt accattagcc gcgacgatag caaaaacacc     240
ctgtacctgc aaatgaacag cctgaaaacc gaagataccg ccgtgtatta ttgcgcgcgt     300
ggtcgttacc ctgagctggg atacttcgat ctgtggggcc agggcaccct ggttactgtc     360
tcgagc                                                                366

<210> SEQ ID NO 54
<211> LENGTH: 339
<212> TYPE: DNA
<213> ORGANISM: Homo sapiens

<400> SEQUENCE: 54
cagagcgtgc tgacccagcc gccgagcgtt agcgccgcac caggccagaa agtgaccatt      60
agctgtagcg gcagcagcag caacatcggc aacaactacg ttagctggta tcagcagctg     120
ccgggcaccg ccccgaaact gctgatctat gataacaaca acgcccgagc ggcatcccg     180 gatcgcttta gcggtagcaa aagcggcacc agcgccaccc tgggcattac cggcctgcaa     240
```

```
accgaagacg aagccgatta ttactgcggt gcttgggact cttacctgtc tgtttctttc    300
gtgtttggcg gcggtaccaa gctgaccgtg ctgggccag                           339
```

<210> SEQ ID NO 55
<211> LENGTH: 122
<212> TYPE: PRT
<213> ORGANISM: Homo sapiens

<400> SEQUENCE: 55

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Gly Arg Ile Lys Ser Lys Thr Tyr Gly Gly Thr Thr Asp Tyr Ala Glu
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Gly Arg Tyr Pro Glu Leu Gly Tyr Phe Asp Leu Trp
            100                 105                 110

Gly Gln Gly Thr Leu Val Thr Val Ser Ser
        115                 120

<210> SEQ ID NO 56
<211> LENGTH: 113
<212> TYPE: PRT
<213> ORGANISM: Homo sapiens

<400> SEQUENCE: 56

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Glu Asp Glu Ala Asp Tyr Tyr Cys Gly Ala Trp Asp Ser Tyr Leu
                85                  90                  95

Ser Val Ser Phe Val Phe Gly Gly Gly Thr Lys Leu Thr Val Leu Gly
            100                 105                 110

Gln

<210> SEQ ID NO 57
<211> LENGTH: 5
<212> TYPE: PRT
<213> ORGANISM: Homo sapiens

<400> SEQUENCE: 57

Asn Tyr Trp Ile Ser
1               5

<210> SEQ ID NO 58
<211> LENGTH: 19
<212> TYPE: PRT
<213> ORGANISM: Homo sapiens

<400> SEQUENCE: 58

Arg Ile Lys Ser Lys Thr Tyr Gly Gly Thr Thr Asp Tyr Ala Glu Pro
1               5                   10                  15
Val Lys Gly

<210> SEQ ID NO 59
<211> LENGTH: 11
<212> TYPE: PRT
<213> ORGANISM: Homo sapiens

<400> SEQUENCE: 59

Gly Arg Tyr Pro Glu Leu Gly Tyr Phe Asp Leu
1               5                   10

<210> SEQ ID NO 60
<211> LENGTH: 13
<212> TYPE: PRT
<213> ORGANISM: Homo sapiens

<400> SEQUENCE: 60

Ser Gly Ser Ser Ser Asn Ile Gly Asn Asn Tyr Val Ser
1               5                   10

<210> SEQ ID NO 61
<211> LENGTH: 7
<212> TYPE: PRT
<213> ORGANISM: Homo sapiens

<400> SEQUENCE: 61

Asp Asn Asn Lys Arg Pro Ser
1               5

<210> SEQ ID NO 62
<211> LENGTH: 12
<212> TYPE: PRT
<213> ORGANISM: Homo sapiens

<400> SEQUENCE: 62

Gly Ala Trp Asp Ser Tyr Leu Ser Val Ser Phe Val
1               5                   10

<210> SEQ ID NO 63
<211> LENGTH: 9
<212> TYPE: PRT
<213> ORGANISM: Homo sapiens

<400> SEQUENCE: 63

Ile Leu Ser Leu Glu Leu Met Lys Leu
1               5

<210> SEQ ID NO 64
<211> LENGTH: 9
<212> TYPE: PRT
<213> ORGANISM: Homo sapiens

<400> SEQUENCE: 64

Arg Met Phe Pro Gly Glu Val Ala Leu
1               5

ANTI-WT1/HLA-SPECIFIC ANTIBODIES

CROSS REFERENCE TO RELATED APPLICATIONS

This application claims the benefit of U.S. Provisional Application Ser. No. 62/239,438, filed 9 Oct. 2015, Great Britain Application No. 1517913.8, filed 9 Oct. 2015, and European Application No. 15189753.5, filed 14 Oct. 2015, the content of each of these applications is herein incorporated by reference in their entirety.

This application also is related to PCT/EP2016/073587, filed 4 Oct. 2016, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-056001_ST25.txt" created on 7 Oct. 2016, and 29,965 bytes in size) is submitted concurrently with the instant application, and the entire contents of the Sequence Listing are incorporated herein by reference.

FIELD

The present application relates to antibodies or antibody fragments which specifically bind to the WT1/HLA complex. The invention also relates to nucleic acids, vectors and host cells capable of expressing said antibodies or fragments thereof, pharmaceutical compositions comprising said antibodies or fragments thereof and uses of said antibodies or fragments thereof for treatment of specific diseases.

BACKGROUND OF THE INVENTION

The Wilms tumor 1 (WT1) oncoprotein is an intracellular, oncogenic transcription factor that is overexpressed in a wide range of leukemias and solid cancers. WT1 is a nuclear protein and therefore not accessible for conventional antibody therapy. A WT1-derived peptide named RMF (amino acid sequence RMFPNAPYL (SEQ ID No. #1)) is processed and presented by HLA-A0201 molecules. This peptide induces cytotoxic CD8 T cells capable of killing WT1+ tumor cells in vitro and in human T cell-based and vaccine trials (Cancer Immunol Immunother. 2010; 59:1467-1479). This provides a rationale to target the HLA-restricted peptide with antibodies.

Antibodies against the WT1 RMF peptide/HLA-A0201 complex (RMF/HLA) have been described. Dao et al., Sci Transl Med. 2013 Mar. 13; 5(176): 176ra33; WO 2012/135854). Derivatives of these antibodies in bispecific format (WO 2015/070061) and with enhanced Fc-activity (WO 2015/070078) were also generated.

The present invention provides novel antibodies and antibody fragments that are superior to the antibodies known in the prior art. The antibodies and antibody fragments disclosed herein specifically bind to the WT1 RMF peptide/HLA-A0201 complex (RMF/HLA).

These antibodies and antibody fragments are particularly well suited for preclinical and clinical development and represent promising drug candidates. The antibodies are also amenable for further improvements, including those described herein.

SUMMARY OF THE INVENTION

The present application for the first time discloses antibodies and fragments thereof that specifically bind to RMF peptide/HLA-A0201 complex (RMF/HLA) and have the superior properties as disclosed herein. The antibodies and fragments thereof of the present disclosure do not bind to unspecific peptides complexed with HLA-A0201. In particular, the antibodies and fragments thereof of the present disclosure do not bind to the PIGQ peptide (a peptide ubiquitously expressed on healthy human tissue) when complexed with HLA-A0201. The antibodies or fragments thereof of the present invention bind to cells expressing the RMF/HLA complex. In particular, the antibodies of the present invention bind to cancer cells expressing the RMF/HLA complex. The antibodies and fragments thereof also show $EC_{50}$ values and affinities in a monovalent Fab format and in a bispecific immunoglobulin format that have never been reported before. Thus, the antibodies or fragments thereof of the present invention are therefore improved in terms of effectiveness, and thus provide well suited and promising compounds, e.g. for clinical development.

Antibodies with the properties as claimed were generated utilizing a sophisticated screening and counter-screening method. It is therefore possible to identify additional antibodies or fragments thereof having essentially the same or the same properties.

The present invention provides antibodies or fragments thereof that specifically bind to the RMF/HLA complex present on the surface cells. The present disclosure also provides antibodies or fragments thereof that specifically bind to the RMF/HLA complex but which do not bind to the PIGQ/HLA complex. The present disclosure also provides antibodies or fragments thereof that bind to the RMF/HLA complex with an $EC_{50}$ which is at least 10 times lower than the $EC_{50}$ for the PIGQ/HLA complex.

The present invention also relates to a method for identifying an antibody or fragment thereof according to the present invention, comprising (a) mixing an antibody library comprising a plurality of antibodies or fragments thereof with a PIGQ/HLA complex under conditions allowing a specific binding of antibodies or the fragments thereof to said complex, (b) removing from the antibody library those antibodies or fragments thereof that bind to said PIGQ/HLA complex, (c) mixing the depleted antibody library of step (b) with an RMF/HLA complex under conditions allowing a specific binding of antibodies or the fragments thereof to said complex, and (d) identifying those antibodies or fragments thereof that bind to the RMF/HLA complex.

The present invention provides antibodies or fragments thereof that bind to the RMF peptide/HLA-A0201 complex (RMF/HLA) having the CDR regions according to the amino acids as listed in Table 1. The present invention also provides specific antibodies or fragments thereof having a variable heavy chain and a variable light chain comprising the amino acid sequences according to Table 1. The present invention also provides specific antibodies or fragments thereof having CDR regions comprising the amino acid sequences according to Table 1. The present invention also provides antibodies or fragments thereof comprising a heavy chain and a light chain that is at least 60%, at least 70%, at least 80%, at least 90% or at least 95% homologous (identical) to the ones of the antibodies as shown in Table 1. The present invention also provides antibodies or fragments thereof which comprising CDR regions that are at least 60%, at least 70%, at least 80%, at least 90% or at least 95% homologous to the CDR regions of the antibodies as shown in Table 1.

The present invention also provides specific antibodies or fragments thereof the binding of which competes with the specific antibodies or fragments thereof as disclosed herein. The present invention also provides specific antibodies or antibody fragments which bind to the same epitope as the specific antibodies or fragments thereof disclosed herein. The present invention also provides specific antibodies or fragments thereof that compete with the specific antibodies or fragments thereof disclosed herein and specifically bind to the RMF/HLA complex when presented on the surface of cells.

The present invention also provides the isolated antibodies or fragments thereof of the present invention for use in medicine. The present invention also provides the antibodies or fragments thereof of the present invention for use in the treatment of patients suffering from a WT1-positive disease, such as cancer. Such WT1 positive diseases and cancers include chronic myelocytic leukemia (CML), multiple myeloma (MM), acute lymphoblastic leukemia (ALL), acute myeloid/myelogenous leukemia (AML), myelodysplastic syndrome (MDS), mesothelioma, ovarian cancer, gastrointestinal cancers, breast cancer, prostate cancer and glioblastoma. In some embodiments, the antibody or fragment thereof is a conjugate having a cytotoxic moiety linked thereto. In other embodiments, the antibody or fragment thereof can carry certain additional modifications, such as, for example, Fc modifications.

The present invention also provides pharmaceutical compositions comprising the isolated antibodies or fragments thereof of the present invention, and a pharmaceutically acceptable carrier.

The present invention also provides nucleic acids encoding for the antibodies or fragments thereof of the present invention.

The present invention also provides vectors comprising nucleic acids encoding the antibodies or fragments thereof of the present invention.

The present invention also provides host cell comprising vector or nucleic acids encoding the antibodies or fragments thereof of the present invention.

DETAILED DESCRIPTION OF THE INVENTION

The invention relates to antibodies or fragments thereof that recognize, preferably specifically recognize, and thus bind to, WT1 RMF peptide/HLA-A0201 complexes (RMF/HLA).

The term "WT1" refers to a protein known as Wilms tumor protein. Certain synonyms of WT1 do exits, including AWT1, GUD, NPHS4, WAGR, Wilms tumor protein, WIT-2 and WT33. Human WT1 has the following amino acid sequence (UniProt P19544):

(SEQ ID NO: 2)
MGSDVRDLNALLPAVPSLGGGGGCALPVSGAAQWAPVLDFAPPGASAYGS

LGGPAPPPAPPPPPPPPPHSFIKQEPSWGGAEPHEEQCLSAFTVHFSGQF

TGTAGACRYGPFGPPPPSQASSGQARMFPNAPYLPSCLESQPAIRNQGYS

TVTFDGTPSYGHTPSHHAAQFPNHSFKHEDPMGQQGSLGEQQYSVPPPVY

GCHTPTDSCTGSQALLLRTPYSSDNLYQMTSQLECMTWNQMNLGATLKGV

-continued
AAGSSSSVKWTEGQSNHSTGYESDNHTTPILCGAQYRIHTHGVFRGIQDV

RRVPGVAPTLVRSASETSEKRPFMCAYPGCNKRYFKLSHLQMHSRKHTGE

KPYQCDFKDCERRFSRSDQLKRHQRRHTGVKPFQCKTCQRKFSRSDHLKT

HTRTHTGKTSEKPFSCRWPSCQKKFARSDELVRHHNMHQRNMTKLQLAL

Homologues of WT1 are also known from other species, including mouse (UniProt P22561), wild boar (NCBI NP_001001264.1), chimpanzee, cattle, red junglefowl, dog, sheep, Japanese rice fish, rat (UniProt P49952) and zebrafish. In most preferred embodiments, WT1 is human WT1. In other preferred embodiments, WT1 is the protein according to SEQ ID NO: 2.

The terms "RMF" and "RMF peptide" refer to the WT1-derived peptide having the amino acid sequence RMFPNAPYL (SEQ ID NO: 1).

The terms "HLAA0201", "HLA-A*02:01" and "HLA-A0201" refer to a specific HLA serotype. HLA-A0201 is a heterodimeric protein, comprising an alpha chain and a beta chain.

The terms "WT1/HLA complex", "WT1/HLA", "RMF/HLA complex" and "RMF/HLA" are used interchangeably, and refer to a complex of the RMF peptide with HLA-A0201. The antibodies and fragments thereof of the present invention are specific for the WT1/HLA complex.

The terms "RHAMM" and "RHAMM peptide" refer to the peptide with the amino acid sequence ILSLELMKL (SEQ ID No. 63). The terms "RHAMM/HLA complex" and "RHAMM/HLA" refer to a complex of said RHAMM peptide with HLA-A0201.

The terms "PIGQ" and "PIGQ peptide" refer to the peptide with the amino acid sequence RMFPGEVAL (SEQ ID No. 64). This peptide occurs ubiquitously in healthy human tissue.

The terms "PIGQ/HLA complex" and "PIGQ/HLA" refer to a complex of the PIGQ peptide with HLA-A0201.

The term "antibody" as used herein refers to a protein comprising at least two heavy (H) chains and two light (L) chains inter-connected by disulfide bonds which interacts (e.g., by binding, steric hindrance, stabilizing spatial distribution) with an antigen. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology. The term "immunoglobulin format" refers to a full length antibody as defined herein above.

The phrase "antibody fragment" or "fragment thereof", as used herein, refers to one or more portions of an antibody that retain(s) the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH—CH1-VH—CH1) which, together with complementary light chain polypeptides, form a pair of antigen-binding sites (Zapata et al., (1995) Protein Eng. 8:1057-1062; and U.S. Pat. No. 5,641,870). The term "Fab format" refers to a Fab fragment of an antibody.

The term "antigen binding site" refers to the part of the antibody or antibody fragment that comprises the area or part(s) of it that specifically bind(s) to an antigen. An antigen binding site may be provided by one or more antibody variable domains. Preferably, an antigen binding site is comprised within the associated VH and VL of an antibody or fragment thereof.

A "human antibody" or "human antibody fragment", as used herein, includes antibodies and fragment thereof having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., (2000) J Mol Biol 296:57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948.

A "humanized antibody" or "humanized antibody fragment" as defined herein is one that is (i) derived from a non-human source (e.g., a transgenic mouse which bears a heterologous immune system), which antibody is based on a human germline sequence or (ii) CDR-grafted, wherein the CDRs of the variable domain are from a non-human origin, while one or more frameworks of the variable domain are of human origin and the constant domain (if any) is of human origin.

The term "chimeric antibody" or "chimeric antibody fragment" is defined herein as an antibody molecule which has constant antibody regions derived from, or corresponding to, sequences found in one species and variable antibody regions derived from another species. Preferably, the constant antibody regions are derived from, or corresponding to, sequences found in humans, e.g. in the human germ line or somatic cells, and the variable antibody regions (e.g. VH, VL, CDR or FR regions) are derived from sequences found in a non-human animal, e.g. a mammal, such as a mouse, rat, rabbit or hamster.

The term "isolated" refers to a compound, which can be e.g. an antibody or antibody fragment, that is substantially free of other antibodies or antibody fragments having different antigenic specificities. Moreover, an isolated antibody or fragment thereof may be substantially free of other cellular material and/or chemicals. Thus, in some aspects, antibodies provided are isolated antibodies which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "recombinant antibody", as used herein, includes all antibodies that are prepared, expressed, created or segregated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody. In an embodiment, the antibodies and antibody fragment disclosed herein are isolated from the Ylanthia® antibody library as disclosed in U.S. Ser. Nos. 13/321,564 or 13/299,367, which both are incorporated herein by reference in their entireties.

The term "monoclonal antibody" as used herein refers to a preparation of antibody molecules of single molecular composition. A monoclonal antibody composition displays a unique binding site having a unique binding specificity and affinity for particular epitopes.

As used herein, an antibody "binds specifically to", "specifically binds to", is "specific to/for" or "specifically recognizes" an antigen, if such antibody or fragment thereof is able to discriminate between such antigen and one or more reference antigen(s), since binding specificity is not an absolute, but a relative property. The reference antigen(s) may be one or more closely related antigen(s), which are used as reference points, e.g. a mutated of scrambled version of the WT1/HLA complex. In particular, an antibody or antibody fragment that "specifically binds to" the WTA/HLA complex does neither bind to the RHAMM/HLA complex nor to the PIGQ/HLA complex.

In its most general form (and unless specifically defined otherwise), a "specific binding" is referring to the ability of the antibody or fragment thereof to discriminate between an antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability to discriminate between different parts of its target antigen, e.g. different domains or regions of the WT1/HLA complex, or between one or more key amino acid residues or stretches of amino acid residues of the WT1/HLA complex. Preferably, the antibodies or fragment thereof disclosed herein specifically bind a WT1/HLA complex of a mammal, in particular to the human WT1/HLA complex.

The term "avidity" is used to describe the combined strength of multiple bond interactions between proteins. Avidity is distinct from affinity which describes the strength of a single bond. As such, avidity is the combined synergistic strength of bond affinities (functional affinity) rather than the sum of bonds. Whilst each single binding interaction of the two binding sites may be readily broken (depending on the relative affinity), because many binding interactions are present at the same time, transient unbinding of a single site does not allow the molecule to diffuse away, and binding of that site is likely to be reinstated. The overall effect is a synergistic, strong binding of antigen to antibody.

As used herein, the term "affinity" refers to the strength of interaction between the polypeptide and its target at a single site. Within each site, the binding region of the polypeptide interacts through weak non-covalent forces with its target at numerous sites; usually, the more interactions, the stronger the affinity.

The term "$K_D$", as used herein, refers to the dissociation constant, which is obtained from the ratio of $K_d$ to $K_a$ (i.e. $K_d/K_a$) and is expressed as a molar concentration (M). $K_D$ values for antigen binding moieties like e.g. monoclonal antibodies can be determined using methods well established in the art. Methods for determining the $K_D$ of an antigen binding moiety like e.g. a monoclonal antibody are SET (soluble equilibrium titration) or surface plasmon resonance using a biosensor system such as a BIACORE® system or an Octet system (ForteBio). In the present invention, an antibody specific for the WT1/HLA complex typically has a dissociation rate constant ($K_D$) ($k_{off}/k_{on}$) of less than $5\times10^{-2}$ M, less than $10^{-2}$ M, less than $5\times10^{-3}$ M, less than $10^{-3}$ M, less than $5\times10^{-4}$ M, less than $10^{-4}$ M, less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M or lower.

"Cross-competing" or "cross-competes" means the ability of an antibody, antibody fragment or other antigen-binding moiety to interfere with the binding of other antibodies, antibody fragments or antigen-binding moieties to a specific antigen in a standard competitive binding assay. The ability or extent to which an antibody, antibody fragment or other antigen-binding moieties is able to interfere with the binding of another antibody, antibody fragment or antigen-binding moieties to a specific antigen, and, therefore whether it can be said to cross-compete according to the invention, can be determined using standard competition binding assays. One suitable assay involves the use of the BIACORE technology (e.g. by using the BIACORE 3000 instrument (BIACORE, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in WO 2003/48731. Cross-competition is present if the antibody or antibody fragment under investigation reduces the binding of one of the antibodies as described in Table 1 to the WT1/HLA complex by 60% or more, specifically by 70% or more and more specifically by 80% or more and if one of the antibodies as described in Table 1 reduces the binding of said antibody or antibody fragment to the WT1/HLA complex by 60% or more, specifically by 70% or more and more specifically by 80% or more.

The term "epitope" includes any proteinaceous region which is specifically recognized by an antibody or fragment thereof or a T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope. An epitope can comprise those residues to which the antibody binds and may be "linear" or "conformational." The term "linear epitope" refers to an epitope wherein all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformations. In a conformational epitope, the points of interaction occur across amino acid residues on the protein that are separated from one another.

"Binds the same epitope as" means the ability of an antibody, antibody fragment or other antigen-binding moiety to bind to a specific antigen and having the same epitope as the exemplified antibody. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two-dimensional nuclear magnetic resonance.

Compositions of the invention may be used for therapeutic or prophylactic applications. The invention, therefore, includes a pharmaceutical composition containing an inventive antibody (or functional antibody fragment) and a pharmaceutically acceptable carrier or excipient therefore. In a related aspect, the invention provides a method for treating an inflammatory disorder. Such method contains the steps of administering to a subject in need thereof an effective amount of the pharmaceutical composition containing an antibody according to the present invention as described or contemplated herein.

The present invention provides therapeutic methods comprising the administration of a therapeutically effective amount of the WT1/HLA complex antibody as disclosed to a subject in need of such treatment. A "therapeutically effective amount" or "effective amount", as used herein, refers to the amount of the WT1/HLA complex antibody necessary to elicit the desired biological response. In accordance with the present invention, the therapeutically effective amount is the amount of the WT1/HLA complex antibody necessary to treat and/or prevent a specific disease.

"Subject" or "species", as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably, the subject is a primate, most preferably a human.

In one embodiment, the present invention relates to an antibody or fragment thereof that specifically binds to the RMF/HLA complex.

In another embodiment, the present invention relates to an antibody or fragment thereof that specifically binds to the RMF/HLA complex as presented and/or present on the surface of cells.

In another embodiment, the present invention relates to an antibody or fragment thereof which specifically binds to a cell expressing the RMF/HLA complex.

In another embodiment, the present invention relates to an antibody or fragment thereof which specifically binds to a cancer cell expressing the RMF/HLA complex, and preferably to a cancer cell presenting said complex on its surface.

In another embodiment, the present invention relates to an antibody or fragment thereof that binds to the RMF/HLA complex with an EC50 that is at least 10-times lower than the EC50 of said antibody or fragment thereof for the PIGQ/HLA complex.

In another embodiment, the present invention relates to an antibody or fragment thereof that does not bind to the PIGQ/HLA complex.

In another embodiment, the present invention relates to an antibody or fragment thereof that has an EC50 of less than 10 nM in a Fab format and in a immunoglobulin format.

In another embodiment, the present invention relates to an antibody or fragment thereof specific for the WT1/HLA complex, wherein said antibody or fragment thereof comprises the HCDR1 region of SEQ ID NO: 7, the HCDR2 region of SEQ ID NO: 8, the HCDR3 region of SEQ ID NO: 9, the LCDR1 region of SEQ ID NO: 10, the LCDR2 region of SEQ ID NO: 11 and the LCDR3 region of SEQ ID NO: 12.

In another embodiment, the present invention relates to an antibody or fragment thereof specific for the WT1/HLA complex, wherein said antibody or fragment thereof comprises the HCDR1 region of SEQ ID NO: 17, the HCDR2 region of SEQ ID NO: 18, the HCDR3 region of SEQ ID NO: 19, the LCDR1 region of SEQ ID NO: 20, the LCDR2 region of SEQ ID NO: 21 and the LCDR3 region of SEQ ID NO: 22.

In another embodiment, the present invention relates to an antibody or fragment thereof specific for the WT1/HLA complex, wherein said antibody or fragment thereof comprises the HCDR1 region of SEQ ID NO: 27, the HCDR2 region of SEQ ID NO: 28, the HCDR3 region of SEQ ID NO: 29, the LCDR1 region of SEQ ID NO: 30, the LCDR2 region of SEQ ID NO: 31 and the LCDR3 region of SEQ ID NO: 32.

In another embodiment, the present invention relates to an antibody or fragment thereof specific for the WT1/HLA complex, wherein said antibody or fragment thereof comprises the HCDR1 region of SEQ ID NO: 37, the HCDR2 region of SEQ ID NO: 38, the HCDR3 region of SEQ ID NO: 39, the LCDR1 region of SEQ ID NO: 40, the LCDR2 region of SEQ ID NO: 41 and the LCDR3 region of SEQ ID NO: 42.

In another embodiment, the present invention relates to an antibody or fragment thereof specific for the WT1/HLA complex, wherein said antibody or antibody fragment comprises the HCDR1 region of SEQ ID NO: 47, the HCDR2 region of SEQ ID NO: 48, the HCDR3 region of SEQ ID NO: 49, the LCDR1 region of SEQ ID NO: 50, the LCDR2 region of SEQ ID NO: 51 and the LCDR3 region of SEQ ID NO: 52.

In another embodiment, the present invention relates to an antibody or fragment thereof specific for the WT1/HLA complex, wherein said antibody or antibody fragment comprises the HCDR1 region of SEQ ID NO: 57, the HCDR2 region of SEQ ID NO: 58, the HCDR3 region of SEQ ID NO: 59, the LCDR1 region of SEQ ID NO: 60, the LCDR2 region of SEQ ID NO: 61 and the LCDR3 region of SEQ ID NO: 62.

In another embodiment of the present invention, the antibody or fragment thereof specifically binds to the human WT1/HLA complex.

In another embodiment of the present invention, the antibody or fragment thereof is a monoclonal antibody or fragment.

In another embodiment of the present invention the antibody or fragment thereof is a human, humanized or chimeric antibody or fragment thereof. In another embodiment of the present invention the antibody or fragment thereof is of the IgG isotype.

In one embodiment, the present invention relates to an antibody or fragment thereof specific for the WT1/HLA complex, wherein said antibody or fragment thereof comprises a heavy chain of SEQ ID NO: 5, and a light chain of SEQ ID NO: 6. In another embodiment, the present invention relates to an antibody or fragment thereof specific for the WT1/HLA complex, wherein said antibody or fragment thereof comprises a heavy chain and a light chain that has at least 60%, at least 70%, at least 80%, at least 90% or at least 95% identity to the a heavy chain of SEQ ID NO: 5 and to the light chain of SEQ ID NO: 6.

In one embodiment, the present invention relates to an antibody or fragment thereof specific for the WT1/HLA complex, wherein said antibody or fragment thereof comprises a heavy chain of SEQ ID NO: 15 and a light chain of SEQ ID NO: 16. In another embodiment, the present invention relates to an antibody or fragment thereof specific for the WT1/HLA complex, wherein said antibody or fragment thereof comprises a heavy chain and a light chain that has at least 60%, at least 70%, at least 80%, at least 90% or at least 95% identity to the a heavy chain of SEQ ID NO: 15 and to the light chain of SEQ ID NO: 16.

In one embodiment, the present invention relates to an antibody or antibody fragment specific for the WT1/HLA complex, wherein said antibody or fragment thereof comprises a heavy chain of SEQ ID NO: 25 and a light chain of SEQ ID NO: 26. In another embodiment, the present invention relates to an antibody or fragment thereof specific for the WT1/HLA complex, wherein said antibody or fragment thereof comprises a heavy chain and a light chain that has at least 60%, at least 70%, at least 80%, at least 90% or at least 95% identity to the a heavy chain of SEQ ID NO: 25 and to the light chain of SEQ ID NO: 26.

In one embodiment, the present invention relates to an antibody or fragment thereof specific for the WT1/HLA complex, wherein said antibody or fragment thereof comprises a heavy chain of SEQ ID NO: 35 and a light chain of SEQ ID NO: 36. In another embodiment, the present invention relates to an antibody or fragment thereof specific for the WT1/HLA complex, wherein said antibody or fragment thereof comprises a heavy chain and a light chain that has at least 60%, at least 70%, at least 80%, at least 90% or at least 95% identity to the a heavy chain of SEQ ID NO: 35 and to the light chain of SEQ ID NO: 36.

In one embodiment, the present invention relates to an antibody or fragment thereof specific for the WT1/HLA complex, wherein said antibody or fragment thereof comprises a heavy chain of SEQ ID NO: 45 and a light chain of SEQ ID NO: 46. In another embodiment, the present invention relates to an antibody or fragment thereof specific for the WT1/HLA complex, wherein said antibody or fragment thereof comprises a heavy chain and a light chain that has at least 60%, at least 70%, at least 80%, at least 90% or at least 95% identity to the a heavy chain of SEQ ID NO: 45 and to the light chain of SEQ ID NO: 46.

In one embodiment, the present invention relates to an antibody or fragment thereof specific for the WT1/HLA complex, wherein said antibody or fragment thereof comprises a heavy chain of SEQ ID NO: 55 and a light chain of SEQ ID NO: 56. In another embodiment, the present invention relates to an antibody or fragment thereof specific for the WT1/HLA complex, wherein said antibody or fragment thereof comprises a heavy chain and a light chain that has at least 60%, at least 70%, at least 80%, at least 90% or at least 95% identity to the a heavy chain of SEQ ID NO: 55 and to the light chain of SEQ ID NO: 56.

In another embodiment of the present invention, the antibody or fragment thereof is an isolated antibody or fragment thereof.

In another embodiment of the present invention, the antibody or fragment thereof is a recombinant antibody or fragment thereof.

In one embodiment, the present invention relates to an antibody or fragment thereof specific for the WT1/HLA complex for use in the treatment of a WT1-positive disease.

In another embodiment, the present invention relates to an antibody or fragment thereof specific for the WT1/HLA complex for use in the treatment of disease characterized by the undesired presence and/or expression of WT1.

In one embodiment, the present invention relates to a nucleic acid composition comprising a nucleic acid sequence or a plurality of nucleic acid sequences encoding an antibody or fragment thereof that is specific for the WT1/HLA complex, wherein said antibody or fragment thereof comprises the HCDR1 region of SEQ ID NO: 7, the HCDR2 region of SEQ ID NO: 8, the HCDR3 region of SEQ ID NO: 9, the LCDR1 region of SEQ ID NO: 10, the LCDR2 region of SEQ ID NO: 11 and the LCDR3 region of SEQ ID NO: 12; the HCDR1 region of SEQ ID NO: 17, the HCDR2 region of SEQ ID NO: 18, the HCDR3 region of SEQ ID NO: 19, the LCDR1 region of SEQ ID NO: 20, the LCDR2 region of SEQ ID NO: 21 and the LCDR3 region of SEQ ID NO: 22; the HCDR1 region of SEQ ID NO: 27, the HCDR2 region of SEQ ID NO: 28, the HCDR3 region of SEQ ID NO: 29, the LCDR1 region of SEQ ID NO: 30, the LCDR2 region of SEQ ID NO: 31 and the LCDR3 region of SEQ ID NO: 32; the HCDR1 region of SEQ ID NO: 37, the HCDR2 region of SEQ ID NO: 38, the HCDR3 region of SEQ ID NO: 39, the LCDR1 region of SEQ ID NO: 40, the LCDR2 region of SEQ ID NO: 41 and the LCDR3 region of SEQ ID NO: 42; the HCDR1 region of SEQ ID NO: 47, the HCDR2 region of SEQ ID NO: 48, the HCDR3 region of SEQ ID NO: 49, the LCDR1 region of SEQ ID NO: 50, the LCDR2 region of SEQ ID NO: 51 and the LCDR3 region of SEQ ID NO: 52; or the HCDR1 region of SEQ ID NO: 57, the HCDR2 region of SEQ ID NO: 58, the HCDR3 region of SEQ ID NO: 59, the LCDR1 region of SEQ ID NO: 50, the LCDR2 region of SEQ ID NO: 51 and the LCDR3 region of SEQ ID NO: 52.

In one embodiment, the present invention relates to a nucleic acid molecule comprising at least one of (a) the variable heavy chain DNA sequence of SEQ ID NO: 3 and the variable light chain DNA sequence of SEQ ID NO: 4;

(b) the variable heavy chain DNA sequence of SEQ ID NO: 13 and the variable light chain DNA sequence of SEQ ID NO: 14;

(c) the variable heavy chain DNA sequence of SEQ ID NO: 23 and the variable light chain DNA sequence of SEQ ID NO: 24;

(d) the variable heavy chain DNA sequence of SEQ ID NO: 33 and the variable light chain DNA sequence of SEQ ID NO: 34;

(e) the variable heavy chain DNA sequence of SEQ ID NO: 43 and the variable light chain DNA sequence of SEQ ID NO: 44; or (f) the variable heavy chain DNA sequence of SEQ ID NO: 53 and the variable light chain DNA sequence of SEQ ID NO: 54.

In one embodiment, the present invention relates to two nucleic acid molecules, wherein one nucleic acid molecule comprises the DNA sequence of SEQ ID NO: 3, and the second nucleic acid molecule comprises the DNA sequence of SEQ ID NO: 4;

one nucleic acid molecule comprises the DNA sequence of SEQ ID NO: 13, and the second nucleic acid molecule comprises the DNA sequence of SEQ ID NO: 14;

one nucleic acid molecule comprises the DNA sequence of SEQ ID NO: 23, and the second nucleic acid molecule comprises the DNA sequence of SEQ ID NO: 24;

one nucleic acid molecule comprises the DNA sequence of SEQ ID NO: 33, and the second nucleic acid molecule comprises the DNA sequence of SEQ ID NO: 34;
one nucleic acid molecule comprises the DNA sequence of SEQ ID NO: 43, and the second nucleic acid molecule comprises the DNA sequence of SEQ ID NO: 44; or
one nucleic acid molecule comprises the DNA sequence of SEQ ID NO: 53, and the second nucleic acid molecule comprises the DNA sequence of SEQ ID NO: 54.

In another embodiment, the present invention relates to a vector composition comprising a vector or a plurality of vectors comprising the nucleic acid sequence or plurality of nucleic acid sequences encoding an antibody or fragment thereof as disclosed in Table 1.

In one embodiment, the present invention relates to a cell comprising a vector composition comprising a vector or a plurality of vectors comprising the nucleic acid sequence or plurality of nucleic acid sequences encoding an antibody or fragment thereof as disclosed in Table 1.

In another embodiment, the present invention relates to a pharmaceutical composition comprising an antibody or antibody fragment as disclosed in Table 1 and a pharmaceutically acceptable carrier or excipient.

In one embodiment, said antibody or fragment thereof specifically binds to the RMF/HLA complex and has an EC50 of less than 100 nM, 75 nM, 50 nM, 25 nM, 20 nM, 10 nM, 5 nM, 2.5 nM or 1 nM in a Fab format. In preferred embodiments, said antibody or fragment thereof specifically binds to the RMF/HLA complex and has an EC50 of less than 10 nm in a Fab format.

In one embodiment, said antibody or fragment thereof specifically binds to the RMF/HLA complex and has an EC50 of less than 100 nM, 75 nM, 50 nM, 25 nM, 20 nM, 10 nM, 5 nM, 2.5 nM or 1 nM in an immunoglobulin format. In preferred embodiments, said antibody or fragment thereof specifically binds to the RMF/HLA complex and has an EC50 of less than 10 nm in an immunoglobulin format.

In one embodiment, said antibody or fragment thereof specifically binds to the RMF/HLA complex and has an EC50 of less than 100 nM, 75 nM, 50 nM, 25 nM, 20 nM, 10 nM, 5 nM, 2.5 nM or 1 nM in a Fab format and in an immunoglobulin format. In preferred embodiments, said antibody or fragment thereof specifically binds to the RMF/HLA complex and has an EC50 of less than 10 nm in a Fab format and in an immunoglobulin format.

In one embodiment, said antibody or fragment thereof binds to the RMF/HLA complex with an EC50 which is at least 25 times, at least 15 times, at least 10 times or at least 5 times lower than the EC50 for the PIGQ/HLA complex.

In one embodiment, said antibody or fragment thereof binds to the RMF/HLA complex with an EC50 which is at least 25 times, at least 15 times, at least 10 times or at least 5 times lower than the EC50 for the PIGQ/HLA complex in a Fab format.

In one embodiment, said antibody or fragment thereof binds to the RMF/HLA complex with an EC50 which is at least 25 times, at least 15 times, at least 10 times or at least 5 times lower than the EC50 for the PIGQ/HLA complex in an immunoglobulin format.

In one embodiment, said antibody or fragment thereof binds to the RMF/HLA complex with an EC50 which is at least 25 times, at least 15 times, at least 10 times or at least 5 times lower than the EC50 for the PIGQ/HLA complex in a Fab format and in an immunoglobulin format.

In certain embodiments, the EC50 values of the instant applications are EC50 values as measures in ELISA assays.

In certain embodiments, the EC50 values of the instant applications are EC50 values as measures in ELISA assays as exemplified herein.

In one embodiment, said antibody or fragment thereof binds to the RMF/HLA complex, but does not bind to the PIGQ/HLA complex.

In one embodiment the present antibody or fragment thereof specific for the RMF/HLA complex is a monoclonal antibody or antibody fragment.

In one embodiment the present antibody or fragment thereof specific for the RMF/HLA complex is a human, humanized or chimeric antibody. In certain embodiments, said antibody or fragment thereof specific for the RMF/HLA complex is an isolated antibody or fragment thereof. In another embodiment said antibody or fragment thereof is a recombinant antibody or fragment thereof. In a further embodiment, said antibody or fragment thereof is a recombinant human antibody or fragment thereof. In a further embodiment said recombinant human antibody or fragment thereof is an isolated recombinant human antibody or fragment thereof. In a further embodiment said recombinant human antibody or fragment thereof or isolated recombinant human antibody or fragment thereof is monoclonal.

In another embodiment the present antibody or fragment thereof comprises a heavy chain encoded by SEQ ID NO: 13 and a light chain encoded by SEQ ID NO: 14, or a heavy chain encoded by SEQ ID NO: 23 and a light chain encoded by SEQ ID NO: 24, or a heavy chain encoded by SEQ ID NO: 33 and a light chain encoded by SEQ ID NO: 34, or a heavy chain encoded by SEQ ID NO: 43 and a light chain encoded by SEQ ID NO: 44, or a heavy chain encoded by SEQ ID NO: 53 and a light chain encoded by SEQ ID NO: 54, or a heavy chain encoded by SEQ ID NO: 63 and a light chain encoded by SEQ ID NO: 64, or a heavy chain and a light chain that has at least 60%, at least 70%, at least 80%, at least 90% or at least 95% homology aforementioned sequences.

In one embodiment the present antibody or fragment thereof comprises a human heavy chain constant region and a human light chain constant region. In a further embodiment said human heavy chain constant region comprises the amino acid sequences of SEQ ID NO: 5 and the human light chain constant region comprises the amino acid sequences of SEQ ID NO: 6, or said human heavy chain constant region comprises the amino acid sequences of SEQ ID NO: 15 and the human light chain constant region comprises the amino acid sequences of SEQ ID NO: 16, or said human heavy chain constant region comprises the amino acid sequences of SEQ ID NO: 25 and the human light chain constant region comprises the amino acid sequences of SEQ ID NO: 26, or said human heavy chain constant region comprises the amino acid sequences of SEQ ID NO: 35 and the human light chain constant region comprises the amino acid sequences of SEQ ID NO: 36, or said human heavy chain constant region comprises the amino acid sequences of SEQ ID NO: 45 and the human light chain constant region comprises the amino acid sequences of SEQ ID NO: 46, or said human heavy chain constant region comprises the amino acid sequences of SEQ ID NO: 55 and the human light chain constant region comprises the amino acid sequences of SEQ ID NO: 56.

In one embodiment, the disclosed antibody or fragment thereof is of the IgG isotype. In another embodiment said antibody is IgG1.

In one embodiment, the antibody fragment is a bivalent antibody fragment.

In another embodiment, the present invention relates to an antibody or fragment thereof that cross-competes with an antibody described in Table 1. In one embodiment the present invention relates to an antibody or fragment thereof, wherein said antibody or fragment thereof cross-competes with an antibody or fragment thereof comprising 6 CDRs defined by Kabat of one of the antibodies in Table 1.

In another embodiment the present invention relates to an antibody or fragment thereof, wherein said antibody or fragment thereof cross-competes with an antibody or fragment thereof comprising 6 CDRs, wherein the HCDR1 is the amino acid sequence of SEQ ID NO: 7, the HCDR2 is the amino acid sequence of SEQ ID NO: 8, the HCDR3 is the amino acid sequence of SEQ ID NO: 9, the LCDR1 is the amino acid sequence of SEQ ID NO: 10, the LCDR2 is the amino acid sequence of SEQ ID NO: 11 and the LCDR3 is the amino acid sequence of SEQ ID NO: 12. In another embodiment the present invention relates to an antibody or fragment thereof, wherein said antibody or fragment thereof cross-competes with an antibody or fragment thereof comprising the VH according to SEQ ID NO: 5 and the VL according to SEQ ID NO: 6.

In another embodiment the present invention relates to an antibody or fragment thereof, wherein said antibody or fragment thereof cross-competes with an antibody or fragment thereof comprising 6 CDRs, wherein the HCDR1 is the amino acid sequence of SEQ ID NO: 17, the HCDR2 is the amino acid sequence of SEQ ID NO: 18, the HCDR3 is the amino acid sequence of SEQ ID NO: 19, the LCDR1 is the amino acid sequence of SEQ ID NO: 20, the LCDR2 is the amino acid sequence of SEQ ID NO: 21 and the LCDR3 is the amino acid sequence of SEQ ID NO: 22. In another embodiment the present invention relates to an antibody or fragment thereof, wherein said antibody or fragment thereof cross-competes with an antibody or fragment thereof comprising the VH according to SEQ ID NO: 15 and the VL according to SEQ ID NO: 16.

In another embodiment the present invention relates to an antibody or fragment thereof, wherein said antibody or fragment thereof cross-competes with an antibody or fragment thereof comprising 6 CDRs, wherein the HCDR1 is the amino acid sequence of SEQ ID NO: 27, the HCDR2 is the amino acid sequence of SEQ ID NO: 28, the HCDR3 is the amino acid sequence of SEQ ID NO: 29, the LCDR1 is the amino acid sequence of SEQ ID NO: 30, the LCDR2 is the amino acid sequence of SEQ ID NO: 31 and the LCDR3 is the amino acid sequence of SEQ ID NO: 32. In another embodiment the present invention relates to an antibody or fragment thereof, wherein said antibody or fragment thereof cross-competes with an antibody or fragment thereof comprising the VH according to SEQ ID NO: 25 and the VL according to SEQ ID NO: 26.

In another embodiment the present invention relates to an antibody or fragment thereof, wherein said antibody or fragment thereof cross-competes with an antibody or fragment thereof comprising 6 CDRs, wherein the HCDR1 is the amino acid sequence of SEQ ID NO: 37, the HCDR2 is the amino acid sequence of SEQ ID NO: 38, the HCDR3 is the amino acid sequence of SEQ ID NO: 39, the LCDR1 is the amino acid sequence of SEQ ID NO: 40, the LCDR2 is the amino acid sequence of SEQ ID NO: 41 and the LCDR3 is the amino acid sequence of SEQ ID NO: 42. In another embodiment the present invention relates to an antibody or fragment thereof, wherein said antibody or fragment thereof cross-competes with an antibody or fragment thereof comprising the VH according to SEQ ID NO: 35 and the VL according to SEQ ID NO: 36.

In another embodiment the present invention relates to an antibody or fragment thereof, wherein said antibody or fragment thereof cross-competes with an antibody or fragment thereof comprising 6 CDRs, wherein the HCDR1 is the amino acid sequence of SEQ ID NO: 47, the HCDR2 is the amino acid sequence of SEQ ID NO: 48, the HCDR3 is the amino acid sequence of SEQ ID NO: 49, the LCDR1 is the amino acid sequence of SEQ ID NO: 50, the LCDR2 is the amino acid sequence of SEQ ID NO: 51 and the LCDR3 is the amino acid sequence of SEQ ID NO: 52. In another embodiment the present invention relates to an antibody or fragment thereof, wherein said antibody or fragment thereof cross-competes with an antibody or fragment thereof comprising the VH according to SEQ ID NO: 45 and the VL according to SEQ ID NO: 46.

In another embodiment the present invention relates to an antibody or fragment thereof, wherein said antibody or fragment thereof cross-competes with an antibody or fragment thereof comprising 6 CDRs, wherein the HCDR1 is the amino acid sequence of SEQ ID NO: 57, the HCDR2 is the amino acid sequence of SEQ ID NO: 58, the HCDR3 is the amino acid sequence of SEQ ID NO: 59, the LCDR1 is the amino acid sequence of SEQ ID NO: 60, the LCDR2 is the amino acid sequence of SEQ ID NO: 61 and the LCDR3 is the amino acid sequence of SEQ ID NO: 62. In another embodiment the present invention relates to an antibody or fragment thereof, wherein said antibody or fragment thereof cross-competes with an antibody or fragment thereof comprising the VH according to SEQ ID NO: 55 and the VL according to SEQ ID NO: 56.

In a certain embodiment, the invention relates to an antibody or fragment thereof that cross-competes with an antibody described in Table 1 and reduces the specific binding of one of the antibodies described in Table 1 by at least 70%, 80% or 90% in an ELISA-based cross-competition assay. In a certain embodiment, the present invention relates to an monoclonal antibody or fragment thereof that cross-competes with an antibody described in Table 1 and reduces the specific binding of one of the antibodies described in Table 1 to the RMF/HLA complex by at least 70%, 80% or 90% in an ELISA-based cross-competition assay. A representative assay set-up is illustrated in Example 6 of the present invention.

In another embodiment, the present invention relates to an antibody or fragment thereof that binds to (e.g., by binding, stabilizing, spatial distribution) the same epitope as one of the antibodies in Table 1. In a further embodiment said antibody or fragment thereof bind to (e.g., by binding, stabilizing, spatial distribution) the same epitope as an antibody or fragment thereof comprising 6 CDRs defined by Kabat of one of the antibodies in Table 1.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the OMIGA version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157: 105-132; for hydropathy plots.

In one embodiment, the present invention relates to an antibody or fragment thereof comprising 6 CDRs defined by Kabat of any of the antibodies in Table 1. In another aspect, the invention pertains to an isolated monoclonal antibody or fragment thereof comprising 6 CDRs defined by Kabat of each of the antibodies in Table 1.

In another embodiment, the present invention relates to antibodies or fragment thereof specific for the RMF/HLA complex, wherein said antibodies or fragment thereof have a monovalent affinity to the RMF/HLA complex with a dissociation rate constant ($K_D$) of less than $5 \times 10^{-2}$ M, less than $10^{-2}$ M, less than $5 \times 10^{-3}$ M, less than $10^{-3}$ M, less than $5 \times 10^{-4}$ M, less than $10^{-4}$ M, less than $5 \times 10^{-5}$ M, less than $10^{-5}$ M, less than $5 \times 10^{-6}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, less than $10^{-11}$ M, less than $5 \times 10^{-12}$ M, less than $10^{-12}$ M, less than $5 \times 10^{-13}$ M, less than $10^{-13}$ M, less than $5 \times 10^{-14}$ M, less than $10^{-14}$ M, less than $5 \times 10^{-15}$ M, or less than $10^{-15}$ M and wherein said antibodies or fragment thereof in a bivalent format have an affinity (apparent affinity) to the RMF/HLA complex with a dissociation rate constant ($K_D$) which is at least 2-fold, 5-fold, 10-fold, 100-fold, 1000-fold, 10000-fold, 100000-fold lower than the dissociation rate constant (KD) in a monovalent format. In a further embodiment the bivalent affinity of said antibodies or fragments thereof is determined in an IgG-format, wherein the monovalent affinity of said antibodies or fragments thereof is determined in a Fab-format.

In another embodiment the present invention relates to the use of said pharmaceutical composition for the treatment of a disorder or condition associated with the undesired presence and/or expression of WT1. In another embodiment said condition associated with the undesired presence and/or expression of WT1 is cancer.

Such carriers, diluents and excipients are well known in the art, and the skilled artisan will find a formulation and a route of administration best suited to treat a subject with the RMF/HLA antibodies or antibody fragments of the present disclosure.

In another embodiment, the present invention relates to a method for the prophylaxis of an inflammatory disorder in a subject, said method comprising administering an RMF/HLA complex antagonist to said subject. "Prophylaxis" as used in this context refers to methods which aim to prevent the onset of a disease or which delay the onset of a disease.

In some embodiments, the subject is a human. In alternative aspects, the subject is a rodent, such as a rat or a mouse.

In some embodiments, the antibodies or fragments thereof specific for RMF/HLA of the present invention are administered subcutaneously. In other aspects the antibodies or fragments thereof specific for the RMF/HLA complex of the present invention are administered intra-venously, intra-articularly or intra-spinally.

In one embodiment, the invention pertains to an isolated monoclonal antibody or fragment thereof, comprising a VH and a VL of any of the antibodies in Table 1.

In another embodiment, the invention relates to a nucleic acid encoding an isolated monoclonal antibody or fragment thereof, wherein the nucleic acid comprises a VH and a VL of any of the antibodies in Table 1.

TABLE 1

Sequences of the antibodies of the invention

| Antibody# | | SEQ ID NO: | [aa]/DNA |
|---|---|---|---|
| "Aali" | VH (VH3-11) | SEQ ID NO: 3 | CAGGTGCAGCTGGTGGAAAGCGGCGGTGGCCTGGTGAAA CCAGGCGGTAGCCTGCGCCTGAGCTGCGCCGCCAGCGGC TTTACCTTTAGCGATCATTACATTAGCTGGATTCGCCAG GCCCCAGGCAAAGGCCTGGAATGGGTTAGCTATATTAGC AGCAGTGGCAGCACCACCTATTACGCCGAGAGCGTGAAA GGCCGCTTTACCATTAGCCGCGATAACGCCAAAAACAGC CTGTATCTGCAAATGAACAGCCTGCGGGCCGAAGATACC GCCGTGTATTATTGCGCGCGTACTTACGCATATCGTTAC GATTTTGATCTGTGGGGCCAGGGCACCCTGGTTACTGTC TCGAGC |
| | VL (lambda1-40) | SEQ ID NO: 4 | CAGAGCGTGCTGACCCAGCCACCAAGCGTGAGCGGTGCA CCAGGTCAGCGCGTGACCATTAGCTGCACCGGCAGCAGC AGCAACATTGGCGCAGGCTATGATGTGCATTGGTATCAG CAGCTGCCAGGCACCGCACCGAAACTGCTGATTTATGGC AACAGCAATCGCCCAAGCGGTGTGCCGGATCGCTTTAGC GGCAGCAAAAGCGGCACCAGCGCCAGCCTGGCGATTACC GGTCTGCAAGCCGAAGACGAAGCCGATTATTACTGCCAG ACTTGGGTTCATTCTTACTCTACTCCGGTGTTTGGCGGC GGTACCAAGCTGACCGTGCTGGGCCAG |
| | VH | SEQ ID NO: 5 | QVQLVESGGGLVKPGGSLRLSCAASGFTFSDHYISWIRQ APGKGLEWVSYISSSGSTTYYAESVKGRFTISRDNAKNS LYLQMNSLRAEDTAVYYCARTYAYRYDFDLWGQGTLVTV SS |

TABLE 1-continued

Sequences of the antibodies of the invention

| Antibody# | | SEQ ID NO: | [aa]/DNA |
|---|---|---|---|
| | VL | SEQ ID NO: 6 | QSVLTQPPSVSGAPGQRVTISCTGSSSNIGAGYDVHWYQ QLPGTAPKLLIYGNSNRPSGVPDRFSGSKSGTSASLAIT GLQAEDEADYYCQTWVHSYSTPVFGGGTKLTVLGQ |
| | HCDR1 | SEQ ID NO: 7 | DHYIS |
| | HCDR2 | SEQ ID NO: 8 | YISSSGSTTYYAESVKG |
| | HCDR3 | SEQ ID NO: 9 | TYAYRYDFDL |
| | LCDR1 | SEQ ID NO: 10 | TGSSSNIGAGYDVH |
| | LCDR2 | SEQ ID NO: 11 | GNSNRPS |
| | LCDR3 | SEQ ID NO: 12 | QTWVHSYSTPV |
| "Bibi" | VH (VH3-11) | SEQ ID NO: 13 | GAAGTGCAGCTGGTGGAAAGCGGCGGTGGCCTGGTGAAA CCAGGCGGTAGCCTGCGCCTGAGCTGCGCCGCCAGCGGC TTTACCTTTAGCAGCTATAGCATGAACTGGGTTCGCCAG GCCCCAGGCAAAGGCCTGGAATGGGTTAGCAGCATCAGC AGCAGTAGCAGCTATATCTATTACGCCGATAGCGTGAAA GGCCGCTTTACCATTAGCCGCGATAACGCCAAAAACAGC CTGTATCTGCAAATGAACAGCCTGCGGGCCGAAGATACC GCCGTGTATTATTGCGCGCGAACTGAGAGCGTTTGGCAC CTGGGTTTCGATATTTGGGGCCAGGGCACCCTGGTTACT GTCTCGAGC |
| | VL (lambda1-40) | SEQ ID NO: 14 | GATATTCAGATGACCCAGAGCCCGAGCAGCGTTAGCGCC AGCGTGGGCGATCGCGTGACCATTACCTGCCGCGCCAGT CAGGGCATTAGCAGCTGGCTGGCCTGGTATCAGCAGAAA CCGGGCAAAGCCCCGAAACTGCTGATCTATGCCGCCAGC AGCCTGCAAAGCGGCGTGCCAAGTCGCTTTAGCGGCAGC GGTAGCGGCACCGATTTCACCCTGACCATTAGCAGTCTG CAACCGGAAGACTTTGCCACCTATTATTGCCAGCAGAAC CATAAATACCCGATCACCTTCGGCCAGGGTACCAAAGTG GAAATCAAGCGGACC |
| | VH | SEQ ID NO: 15 | EVQLVESGGGLVKPGGSLRLSCAASGFTFSSYSMNWVRQ APGKGLEWVSSISSSSSYIYYADSVKGRFTISRDNAKNS LYLQMNSLRAEDTAVYYCARTESVWHLGFDIWGQGTLVT VSS |
| | VL | SEQ ID NO: 16 | DIQMTQSPSSVSASVGDRVTITCRASQGISSWLAWYQQK PGKAPKLLIYAASSLQSGVPSRFSGSGSGTDFTLTISSL QPEDFATYYCQQNHKYPITFGQGTKVEIKRT |
| | HCDR1 | SEQ ID NO: 17 | SYSMN |
| | HCDR2 | SEQ ID NO: 18 | SISSSSSYIYYADSVKG |
| | HCDR3 | SEQ ID NO: 19 | TESVWHLGFDI |
| | LCDR1 | SEQ ID NO: 20 | RASQGISSWLA |
| | LCDR2 | SEQ ID NO: 21 | AASSLQS |
| | LCDR3 | SEQ ID NO: 22 | QQNHKYPIT |
| "Cyprus" | VH (VH3-11) | SEQ ID NO: 23 | CAGGTGCAGCTGGTGGAAAGCGGCGGTGGCCTGGTGAAA CCAGGCGGTAGCCTGCGCCTGAGCTGCGCCGCCAGCGGC TTTACCTTTAGCGATTACTACATGAGCTGGATTCGCCAG GCCCCAGGCAAAGGCCTGGAATGGGTTAGCTATATTAGC AGCAGTGGCAGCACCATCTATTACGCCGATAGCGTGAAA GGCCGCTTTACCATTAGCCGCGATAACGCCAAAAACAGC CTGTATCTGCAAATGAACAGCCTGCGGGCCGAAGATACC GCCGTGTATTATTGCGCGCGTGACGGACTGCGTTACTTC |

TABLE 1-continued

Sequences of the antibodies of the invention

| Antibody# | | SEQ ID NO: | [aa]/DNA |
|---|---|---|---|
| | | | TATGGATTTGATTACTGGGGCCAGGGCACCCTGGTTACT<br>GTCTCGAGC |
| | VL<br>(lambda1-40) | SEQ ID NO:<br>24 | CAGAGCGTGCTGACCCAGCCGCCGAGCGTTAGCGCCGCA<br>CCAGGCCAGAAAGTGACCATTAGCTGTAGCGGCAGCAGC<br>AGCAACATCGGCAACAACTACGTTAGCTGGTATCAGCAG<br>CTGCCGGGCACCGCCCCGAAACTGCTGATCTATGATAAC<br>AACAAACGCCCGAGCGGCATCCCGGATCGCTTTAGCGGT<br>AGCAAAAGCGGCACCAGCGCCACCCTGGGCATTACCGGC<br>CTGCAAACCGAAGACGAAGCCGATTATTACTGCCAGGCT<br>TGGGTTCATTACTCTCTGGTTCATTGGGTGTTTGGCGGC<br>GGTACCAAGCTGACCGTGCTGGGCCAG |
| | VH | SEQ ID NO:<br>25 | QVQLVESGGGLVKPGGSLRLSCAASGFTFSDYYMSWIRQ<br>APGKGLEWVSYISSSGSTIYYADSVKGRFTISRDNAKNS<br>LYLQMNSLRAEDTAVYYCARDGLRYFYGFDYWGQGTLVT<br>VSS |
| | VL | SEQ ID NO:<br>26 | QSVLTQPPSVSAAPGQKVTISCSGSSSNIGNNYVSWYQQ<br>LPGTAPKLLIYDNNKRPSGIPDRFSGSKSGTSATLGITG<br>LQTEDEADYYCQAWVHYSLVHWVFGGGTKLTVLGQ |
| | HCDR1 | SEQ ID NO:<br>27 | DYYMS |
| | HCDR2 | SEQ ID NO:<br>28 | YISSSGSTIYYADSVKG |
| | HCDR3 | SEQ ID NO:<br>29 | DGLRYFYGFDY |
| | LCDR1 | SEQ ID NO:<br>30 | SGSSSNIGNNYVS |
| | LCDR2 | SEQ ID NO:<br>31 | DNNKRPS |
| | LCDR3 | SEQ ID NO:<br>32 | QAWVHYSLVHWV |
| "Daniel" | VH<br>(VH3-11) | SEQ ID NO:<br>33 | CAGGTGCAGCTGGTGCAGAGCGGTGCCGAAGTGAAAAAA<br>CCAGGCGCCAGCGTGAAAGTTAGCTGCAAAGCCAGCGGC<br>TATACCTTCACCAGCTACTATATGCATTGGGTTCGCCAG<br>GCCCCAGGCCAGGGTCTGGAATGGATGGGCATTATTAAC<br>CCGAGCGGCGGCAGCACCAGCTATGCACAGAAATTTCAG<br>GGCCGCGTGACCATGACCCGCGATACCAGCACCAGCACC<br>GTGTATATGGAACTGAGCAGCCTGCGCAGCGAAGATACC<br>GCCGTGTATTATTGCGCGCGTGAGGGTTACACTCCTGGT<br>GGTAGCTACACTTTCGACATCTGGGGTCAGGGCACCCTG<br>GTTACTGTCTCGAGC |
| | VL<br>(lambda1-40) | SEQ ID NO:<br>34 | CAGAGCGTGCTGACCCAGCCGCCGAGCGTTAGCGCCGCA<br>CCAGGCCAGAAAGTGACCATTAGCTGTAGCGGCAGCAGC<br>AGCAACATCGGCAACAACTACGTTAGCTGGTATCAGCAG<br>CTGCCGGGCACCGCCCCGAAACTGCTGATCTATGATAAC<br>AACAAACGCCCGAGCGGCATCCCGGATCGCTTTAGCGGT<br>AGCAAAAGCGGCACCAGCGCCACCCTGGGCATTACCGGC<br>CTGCAAACCGAAGACGAAGCCGATTATTACTGCGGTTCT<br>TGGGACGGTTTCGTTTCTTCTTACTCTGTGTTTGGCGGC<br>GGTACCAAGCTGACCGTGCTGGGCCAG |
| | VH | SEQ ID NO:<br>35 | QVQLVQSGAEVKKPGASVKVSCKASGYTFTSYYMHWVRQ<br>APGQGLEWMGIINPSGGSTSYAQKFQGRVTMTRDTSTST<br>VYMELSSLRSEDTAVYYCAREGYTPGGSYTFDIWGQGTL<br>VTVSS |
| | VL | SEQ ID NO:<br>36 | QSVLTQPPSVSAAPGQKVTISCSGSSSNIGNNYVSWYQQ<br>LPGTAPKLLIYDNNKRPSGIPDRFSGSKSGTSATLGITG<br>LQTEDEADYYCGSWDGFVSSYSVFGGGTKLTVLGQ |
| | HCDR1 | SEQ ID NO:<br>37 | SYYMH |
| | HCDR2 | SEQ ID NO:<br>38 | IINPSGGSTSYAQKFQG |

TABLE 1-continued

Sequences of the antibodies of the invention

| Antibody# | | SEQ ID NO: | [aa]/DNA |
|---|---|---|---|
| | HCDR3 | SEQ ID NO: 39 | EGYTPGGSYTFDI |
| | LCDR1 | SEQ ID NO: 40 | SGSSSNIGNNYVS |
| | LCDR2 | SEQ ID NO: 41 | DNNKRPS |
| | LCDR3 | SEQ ID NO: 42 | GSWDGFVSSYSV |
| "Elfu" | VH (VH3-11) | SEQ ID NO: 43 | GAAGTGCAGCTGGTGCAGAGCGGTGCCGAAGTGAAAAAA CCCGGGCGAAAGCCTGAAAATCAGCTGCAAAGGCAGCGGC TATAGCTTTACCAGCTATTGGATTAGCTGGGTTCGCCAG ATGCCGGGCAAAGGCCTGGAATGGATGGGCATTATCTAT CCGGGCACCAGCTATACCCGCTATAGCCCGAGCTTTCAG GGCCAGGTTACAATTAGCGCCGACAAAAGCATCAGCACC GCCTATCTGCAATGGAGCAGCCTGAAAGCCAGCGATACC GCCATGTATTATTGCGCGCGAGGATACCACCTGCCTTAC TTTGATTACTGGGGCCAGGGCACCCTGGTTACTGTCTCG AGC |
| | VL (lambda1-40) | SEQ ID NO: 44 | CAGAGCGTGCTGACCCAGCCACCAAGCGTGAGCGGTGCA CCAGGTCAGCGCGTGACCATTAGCTGCACCGGCAGCAGC AGCAACATTGGCGCAGGCTATGATGTGCATTGGTATCAG CAGCTGCCAGGCACCGCACCGAAACTGCTGATTTATGGC AACAGCAATCGCCCAAGCGGTGTGCCGGATCGCTTTAGC GGCAGCAAAAGCGGCACCAGCGCCAGCCTGGCGATTACC GGTCTGCAAGCCGAAGACGAAGCCGATTATTACTGCCAG GCTTACGCTTCTCCGACTCGTGTTGTGTTTGGCGGCGGT ACCAAGCTGACCGTGCTGGGCCAG |
| | VH | SEQ ID NO: 45 | EVQLVQSGAEVKKPGESLKISCKGSGYSFTSYWISWVRQ MPGKGLEWMGIIYPGTSYTRYSPSFQGQVTISADKSIST AYLQWSSLKASDTAMYYCARGYHLPYFDYWGQGTLVTVSS |
| | VL | SEQ ID NO: 46 | QSVLTQPPSVSGAPGQRVTISCTGSSSNIGAGYDVHWYQ QLPGTAPKLLIYGNSNRPSGVPDRFSGSKSGTSASLAIT GLQAEDEADYYCQAYASPTRVVFGGGTKLTVLGQ |
| | HCDR1 | SEQ ID NO: 47 | SYWIS |
| | HCDR2 | SEQ ID NO: 48 | IIYPGTSYTRYSPSFQG |
| | HCDR3 | SEQ ID NO: 49 | GYHLPYFDY |
| | LCDR1 | SEQ ID NO: 50 | TGSSSNIGAGYDVH |
| | LCDR2 | SEQ ID NO: 51 | GNSNRPS |
| | LCDR3 | SEQ ID NO: 52 | QAYASPTRVV |
| "Fiwi" | VH (VH3-11) | SEQ ID NO: 53 | GAAGTGCAGCTGGTGGAAAGCGGCGGTGGCCTGGTGAAA CCAGGCGGTAGCCTGCGCCTGAGCTGCGCCGCCAGCGGC TTTACCTTTAGCAACTATTGGATTAGCTGGGTTCGCCAG GCCCCAGGCAAAGGCCTGGAATGGGTTGGCCGCATCAAA AGCAAAACCTATGGCGGCACCACCGATTATGCCGAGCCA GTGAAAGGCCGCTTTACCATTAGCCGCGACGATAGCAAA AACACCCTGTACCTGCAAATGAACAGCCTGAAAACCGAA GATACCGCCGTGTATTATTGCGCGCGCGTGGTCGTTACCCT GAGCTGGGATACTTCGATCTGTGGGGCCAGGGCACCCTG GTTACTGTCTCGAGC |
| | VL (lambda1-40) | SEQ ID NO: 54 | CAGAGCGTGCTGACCCAGCCGCCGAGCGTTAGCGCCGCA CCAGGCCAGAAAGTGACCATTAGCTGTAGCGGCAGCAGC AGCAACATCGGCAACAACTACGTTAGCTGGTATCAGCAG CTGCCGGGCACCGCCCCGAAACTGCTGATCTATGATAAC AACAAACGCCCGAGCGGCATCCCGGATCGCTTTAGCGGT AGCAAAAGCGGCACCAGCGCCACCCTGGGCATTACCGGC |

TABLE 1-continued

Sequences of the antibodies of the invention

| Antibody# | SEQ ID NO: | [aa]/DNA |
|---|---|---|
|  |  | CTGCAAACCGAAGACGAAGCCGATTATTACTGCGGTGCT TGGGACTCTTACCTGTCTGTTTCTTTCGTGTTTGGCGGC GGTACCAAGCTGACCGTGCTGGGCCAG |
| VH | SEQ ID NO: 55 | EVQLVESGGGLVKPGGSLRLSCAASGFTFSNYWISWVRQ APGKGLEWVGRIKSKTYGGTTDYAEPVKGRFTISRDDSK NTLYLQMNSLKTEDTAVYYCARGRYPELGYFDLWGQGTL VTVSS |
| VL | SEQ ID NO: 56 | QSVLTQPPSVSAAPGQKVTISCSGSSSNIGNNYVSWYQQ LPGTAPKLLIYDNNKRPSGIPDRFSGSKSGTSATLGITG LQTEDEADYYCGAWDSYLSVSFVFGGGTKLTVLGQ |
| HCDR1 | SEQ ID NO: 57 | NYWIS |
| HCDR2 | SEQ ID NO: 58 | RIKSKTYGGTTDYAEPVKG |
| HCDR3 | SEQ ID NO: 59 | GRYPELGYFDL |
| LCDR1 | SEQ ID NO: 60 | SGSSSNIGNNYVS |
| LCDR2 | SEQ ID NO: 61 | DNNKRPS |
| LCDR3 | SEQ ID NO: 62 | GAWDSYLSVSFV |

BRIEF DESCRIPTION OF THE DRAWINGS

The present invention shall now be explained in the following examples with reference to the figures, nevertheless, without being limited thereto. For the purpose of the present invention, all references as cited herein are incorporated by reference in their entireties.

EXAMPLES

Example 1

Generation of Antigens

The RMF/HLA complex was used as a target for antibody selections. The target was produced as described in Dao et al. (Sci Transl Med. 2013 Mar. 13; 5(176): 176ra33). Biotinylated WT1/HLA-A0201 and RHAMM-R3/HLA_A0201 complexes were synthesized by refolding the peptides with recombinant HLA-A2 and β2-microglobulin within the Immunology Department (as described in Altman, et al. 1996. Phenotypic analysis of antigen specific T lymphocytes. Science 274:94, and Jung, G., Ledbetter, J. A., and Müller-Eberhard, H. J. (1987). Induction of cytotoxicity in resting human T lymphocytes bound to tumor cells by antibody heteroconjugates. Proceedings of the National Academy of Sciences of the United States of America, 84(13), 4611-4615, with small modifications).

As a negative control, the RHAMM/HLA complex was generated (Dao et al., 2013). The RHAMM peptide has an amino sequence of ILSLELMKL (SED ID NO: 63). The RHAMM peptide was complexed to HLA-A0201.

As another negative control, a PIGQ/HLA complex was generated. The PIGQ peptide was identified via the XPRESIDENT® (immatics biotechnologies GmbH, Germany) target identification platform (amino acid sequence of RMFPGEVAL (SED ID NO: 64)). It was also complexed to HLA-A0201. The PIGQ peptide occurs ubiquitously in healthy human tissue. Binding to the PIGQ/HLA complex is therefore highly undesirable. Five out of nine amino acids of the PIGQ peptide are identical to the WT1 peptide.

All antigens were produced in biotinylated and in non-biotinylated form. Purity (>95%) and monomer portion (>97-99%) of all peptides and HLA antigens was confirmed via SDS-PAGE, analytical size exclusion chromatography and dynamic light scattering.

Example 2

Generation of Reference Antibodies

Six RMF/HLA complex-binding antibodies are described on WO2012/135854 (Memorial Sloan-Kettering). Five of these six antibodies are also described in the Dao et al. referenced (see above). Only Refmab #18 (see below) is not described in Dao et al. (2013).

The sequences of these six antibodies (Refmab#3, Refmab#5, Refmab#13, Refmab#15, Refmab#18 and Refmab#23) were cloned, and human IgG1f antibodies were produced in HKB11 cells. Antibodies were purified and subjected to quality control (yield, concentration, purity and monomer content).

Example 3

Binding of Reference Antibodies to Isolated Antigens

In this experiment, the specificities of the reference antibodies were investigated. Biotinylated peptide/HLA complexes were coated on NEUTRAVIDIN plates at 50 nM. The isolated reference antibodies of Example 2 were titrated on the antigens: Binding was tested in ELISA utilizing an AP-conjugated goat anti-human IgG secondary antibody.

All reference antibodies bound to the RMF/HLA complex. Refmab#23 also unspecifically bound to the RHAMM-HLA complex, as has been described in the literature.

Figure 1:
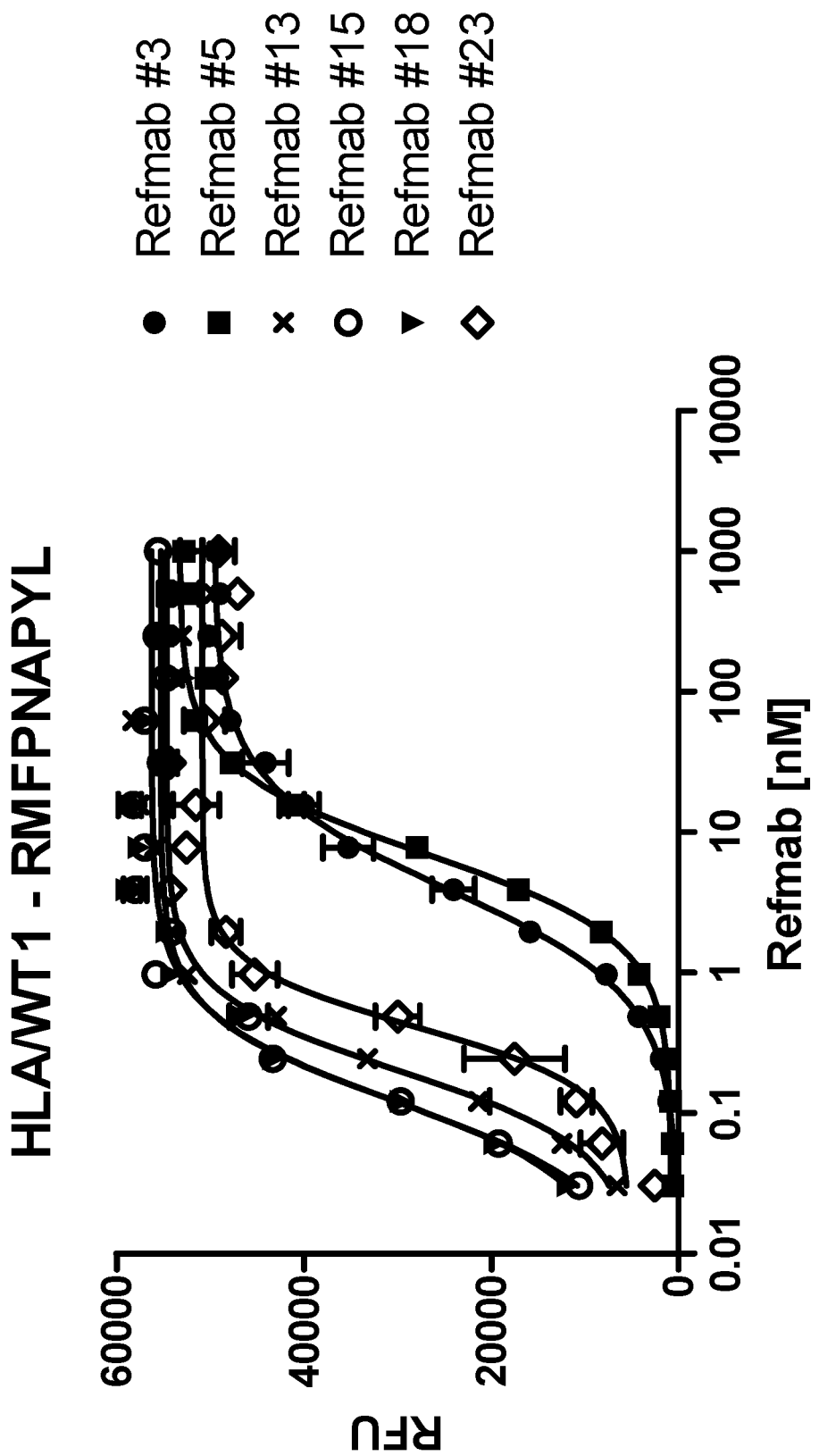
FIG. 1 shows the binding of six reference antibodies to the RMF/HLA complex, i.e., an RMFPNAPYL (SEQ ID NO: 1)/HLA complex.
Figure 2:
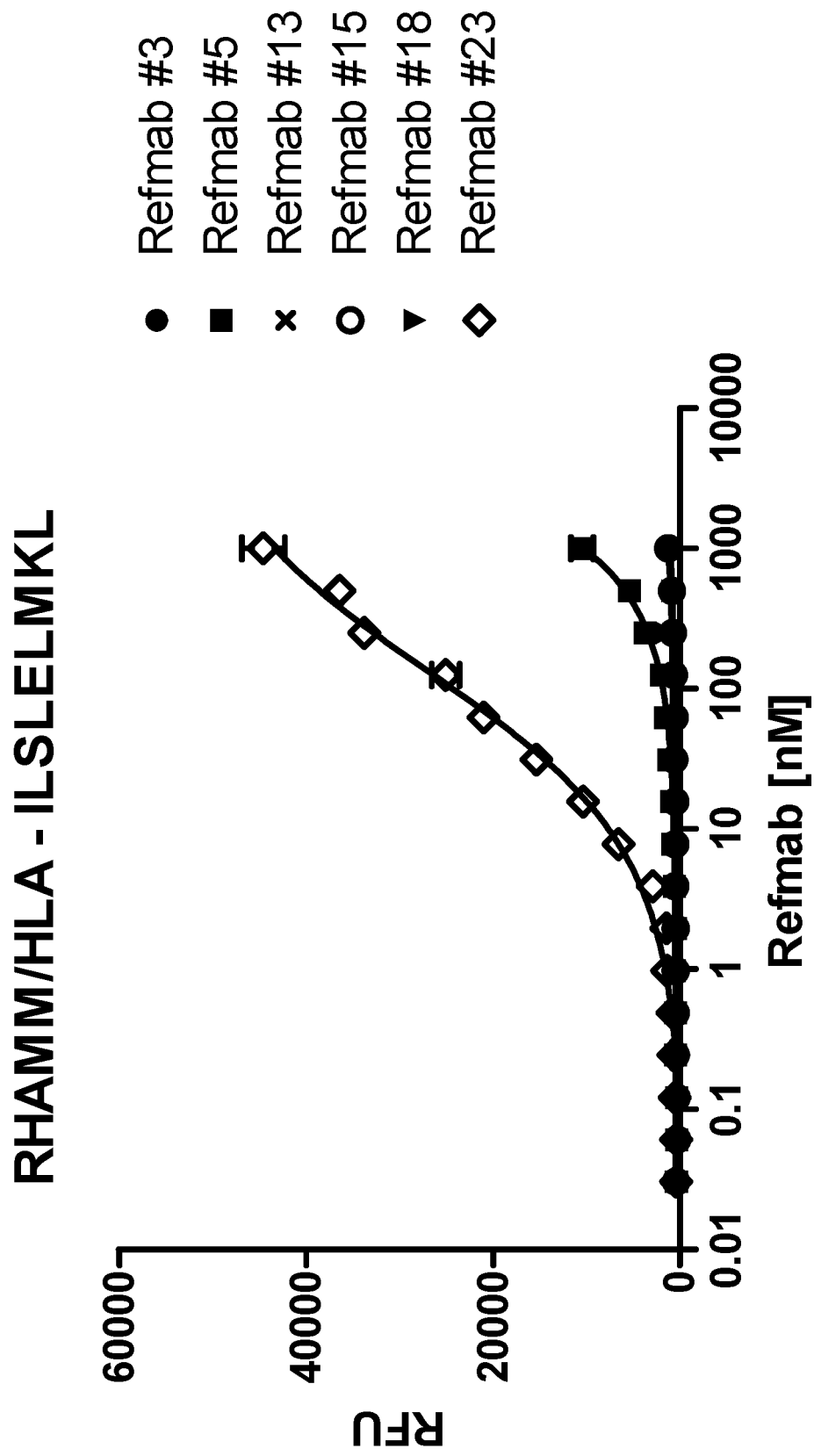
FIG. 2 shows the binding of six reference antibodies to the RHAMM/HLA complex, i.e. an ILSLELMKL (SEQ ID NO: 63)/HLA complex.
Figure 3:
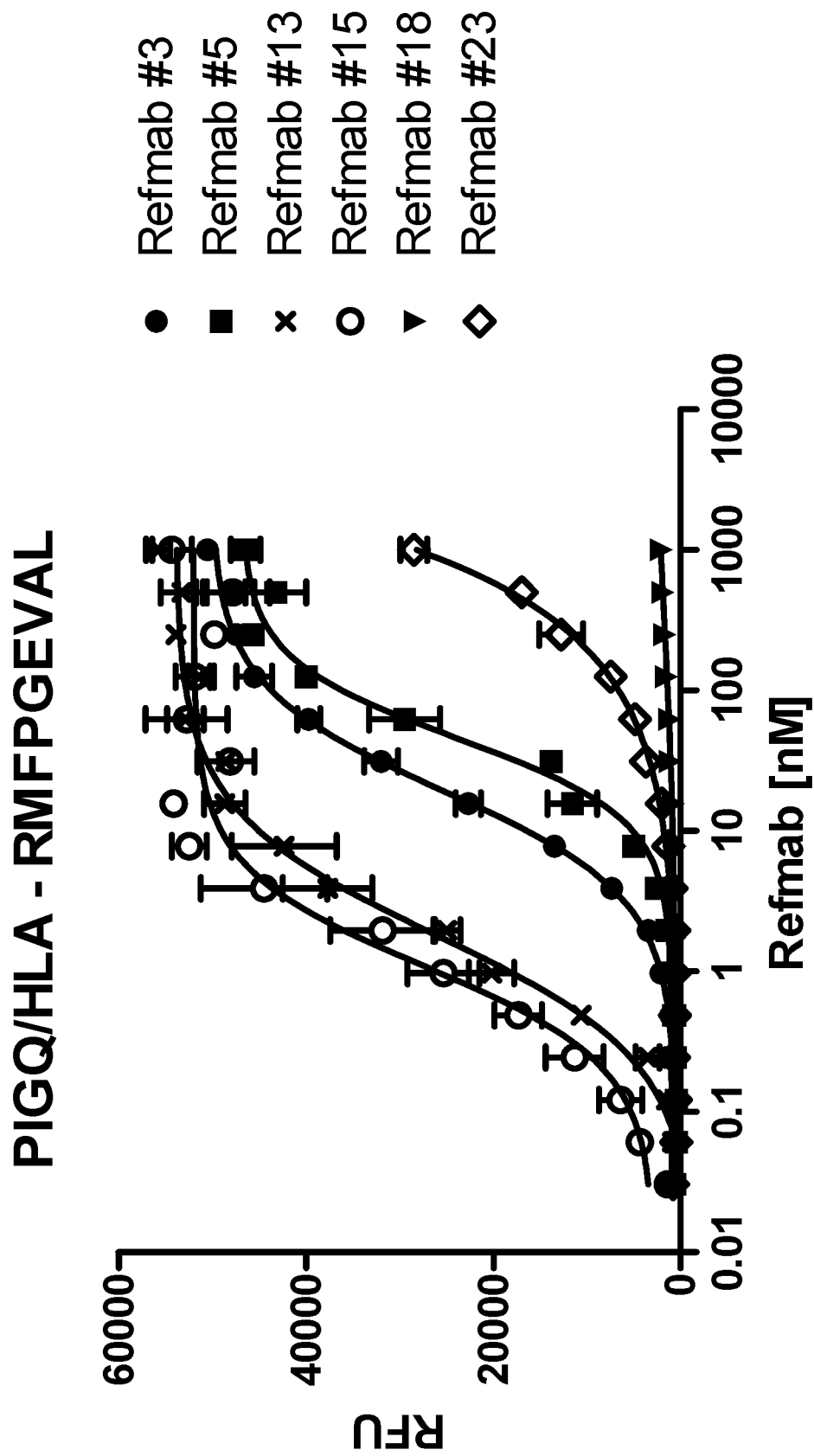
FIG. 3 shows the binding of six reference antibodies to the PIGQ/HLA complex, i.e., an RMFPGEVAL (SEQ ID NO: 64)/HLA complex.

Interestingly all reference antibodies except for Refmab #18 also bound to the PIGQ/HLA complex, i.e. a peptide presented on healthy human tissue. Only Refmab#18 was specific for the WT1-HLA complex in ELISA. Results are shown in FIGS. 1-3.

Example 4

Binding of Reference Antibodies to Antigens on Cells

Since binding to an isolated antigen does not necessarily coincide with binding to the antigen when presented on intact cells it was investigated whether or not the control antibodies also bound to the RMF/HLA complex on cells expressing this antigen.

SET2 cells (DSMZ No. ACC 608) and BV173 cells (DSMZ No. ACC 20) were used as antigen-positive cancer cells (see Dao et al.; 2013). Binding was measured by flow cytometry utilizing a PE-conjugated goat anti-human IgG secondary antibody, and EC50 values were determined. Results are shown in Table 2. "++" designates binding with an EC50 of below 10 nM, "+" designates binding with an EC50 of more than 10 nM, and "---" designates no binding to the target on cells.

TABLE 2

Binding of the reference antibodies (IgG) to cells

| Binder | EC50 on SET2 cells [nM] | EC50 on BV173 cells [nM] |
|---|---|---|
| Refmab #3 | — | — |
| Refmab #5 | + | + |
| Refmab #13 | ++ | ++ |
| Refmab #15 | + | + |
| Refmab #18 | — | — |
| Refmab #23 | + | + |

As can be seen in Table 2, two out of the six reference antibodies do not bind to cells expressing the target. These antibodies (including Refmab #18) are therefore no suitable for therapeutically development.

Example 5

Identification of Superior RMF/HLA Complex Binders

For antibody generation the Ylanthia® library (MorphoSys AG, Germany) was used to select Fab fragments against the WT1/HLA complex. The Ylanthia® library (Tiller et al. mAbs 5:3, 1-26; May/June (2013) and U.S. Pat. No. 8,728, 981) is a commercially available phagemid library and employs the CysDisplay® technology for displaying the Fab on the phage surface (Lohning et al., WO 2001/05950).

In order to isolate RMF/HLA complex-specific antibodies, different panning strategies were used (solution panning, plated-based panning). Each panning strategy comprised at least 3 individual rounds of panning against the RMF/HLA complex. The selection of unspecific binders was inhibited by pre-blocking with the PIGQ/HLA complex as a counter target.

The isolated binders were subjected to primary screening on an INTELLICYT HTFC Screening System utilizing fluorescent beads. Three different antigens (WT1/HLA complex, RHAMM/HLA complex and PIGQ/HLA complex) were tested in parallel. Hits that were positive on the WT1-HLA complex antigen but negative on the other two antigens were isolated and subjected to a secondary screening using a more stringent ELISA assay. A selection of positive clones was converted into IgG format. Six of the most promising candidates were purified and characterized further. The sequences of the six binders are shown in Table 1.

The binders were further subjected to in-depth characterization. They were also directly compared to the antibodies of the prior art. The EC50 of the binders was measured in a monovalent Fab format, and as full-length immunoglobulins (IgG1).

Example 6

Characterization of the Binders in the Fab Format

The binders were subjected to an in-depth characterization. They were directly compared to the antibodies of the prior art in an ELISA assay using NEUTRAVIDIN plates as described in Example 3. For selected reference antibodies and binders of the present invention, the EC50 were determined. Results are summarized in Table 3. "++" designates binding with an EC50 of below 10 nM, "+" designates binding with an EC50 of more than 10 nM, and "---" designates no binding.

The EC50 values on RMF/HLA are significantly lower (better) than the EC50 values of the reference antibodies of the prior art. All binders tested demonstrated an EC50 which was at least 3.3-fold better than that of the best binder of the prior art. Three out of the four binders tested demonstrated an EC50 which was at least 5.5-fold better than that of the best binder of the prior art. Two out of the four binders tested demonstrated an EC50 which was at least 7.5-fold better than that of the best binder in the prior art. Furthermore, none of the binders of the present invention show any binding to the counter targets, in particular no binding to the PIGQ/HLA complex. Some degree of binding was observed for some of the reference antibodies.

Affinities of the Fab fragments of binders Aali and Refmab #13 for the antigen RMF/HLA were also measured with an Octet system using the antigen immobilized to Streptavidin. The KD values were determined as 66 nM for Aali and 590 nM for Refmab #13, also confirming that the antibodies of the present invention have a higher affinity.

TABLE 3

Summary of Fab characterization

| Binder | EC50 on RMF/HLA [nM] | EC50 on RHAMM/HLA [nM] | EC50 on PIGQ/HLA [nM] |
|---|---|---|---|
| "Aali" | ++ | — | — |
| "Cyprus" | ++ | — | — |
| "Daniel" | ++ | — | — |
| "Fiwi" | + | — | — |
| Refmab #3 | + | + | — |
| Refmab #13 | + | — | + |
| Refmab #18 | + | — | — |
| Refmab #23 | + | — | — |

Example 7

Specificity of the Binders in an Immunoglobulin Format

Figure 4:
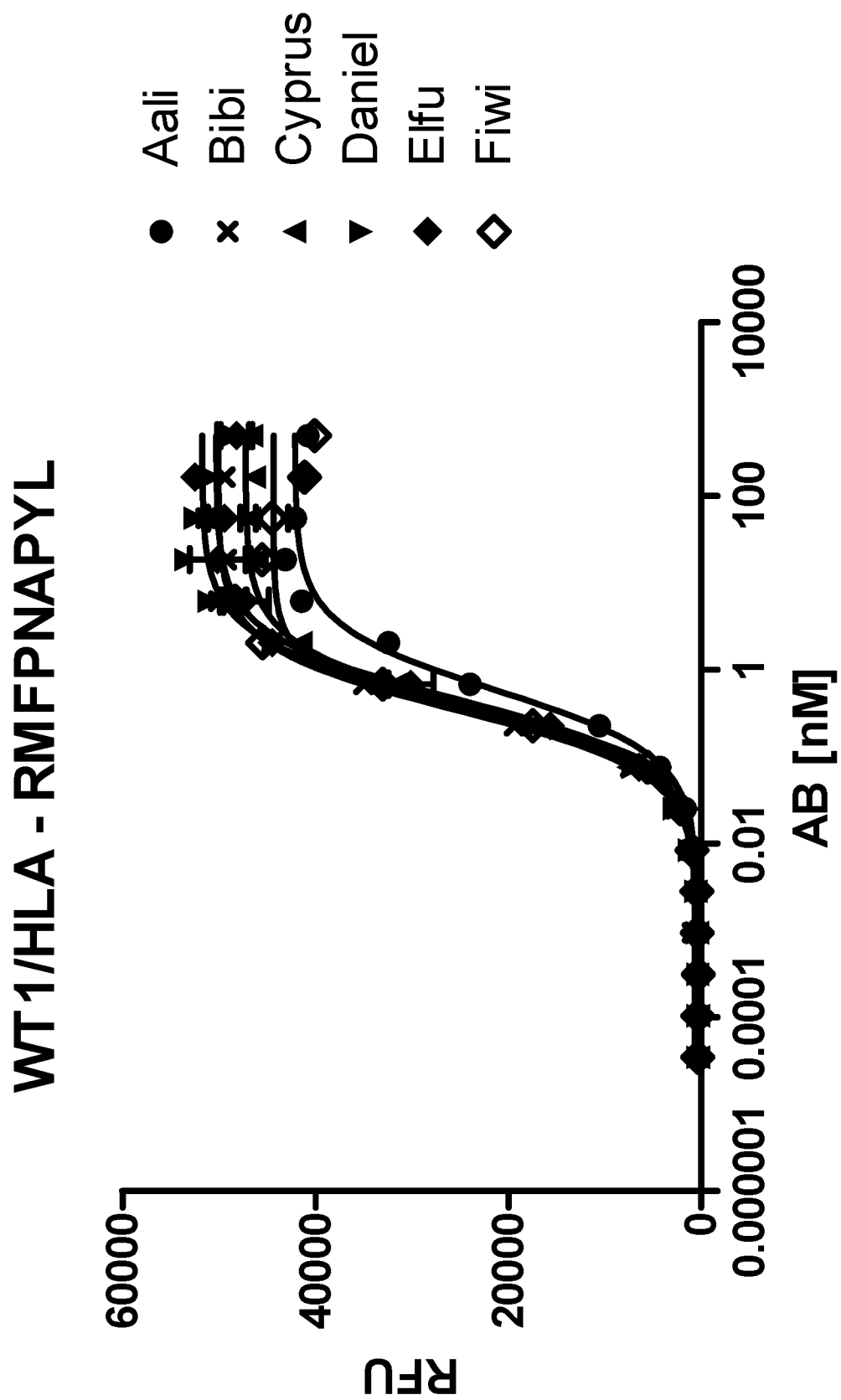
FIG. 4 shows the binding of the antibodies of the present invention to the RMF/HLA complex, i.e., an RMFPNAPYL (SEQ ID NO: 1)/HLA complex.
Figure 5:
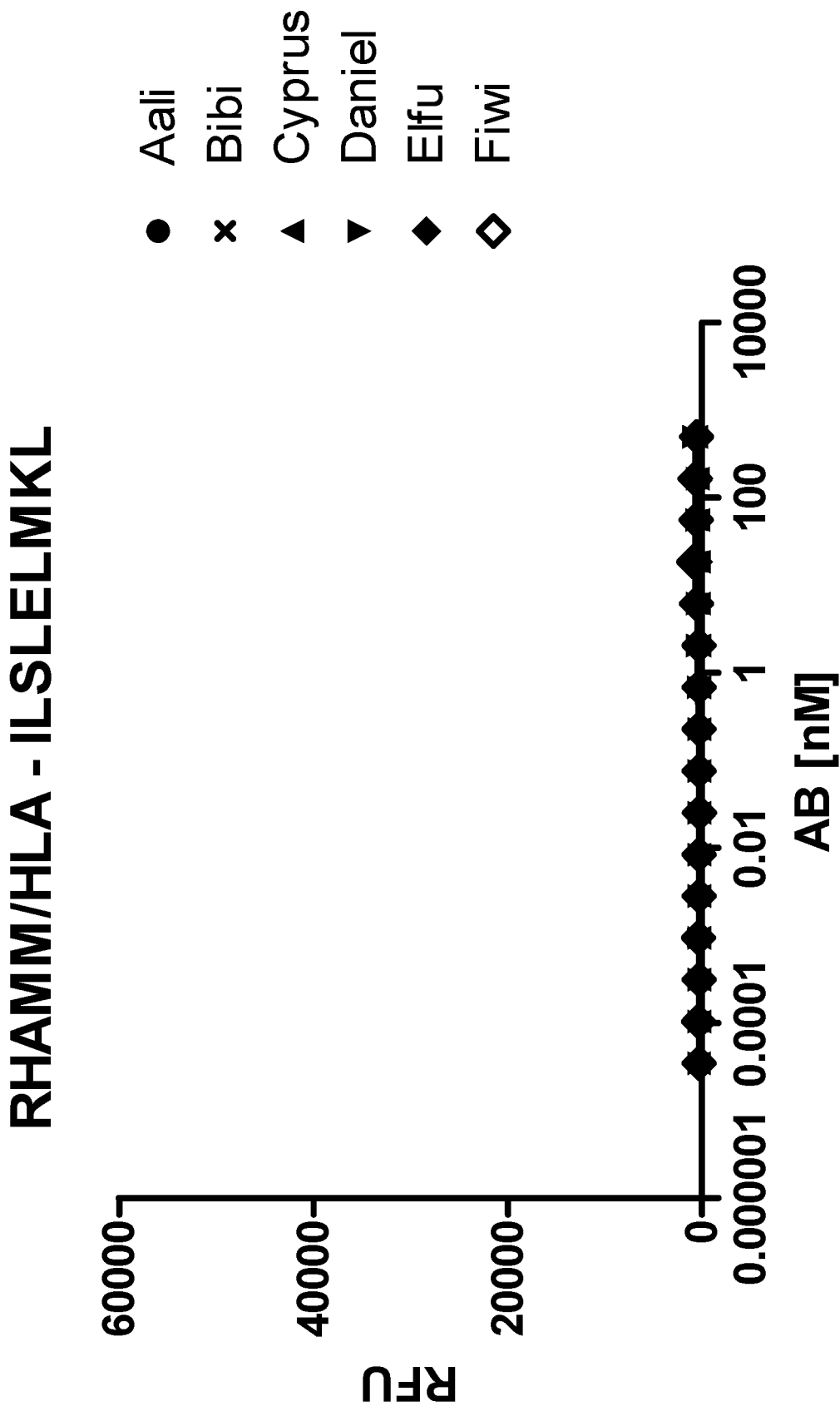
FIG. 5 shows the binding of the antibodies of the present invention to the RHAMM/HLA complex, i.e., an ILSLELMKL (SEQ ID NO: 63)/HLA complex.
Figure 6:
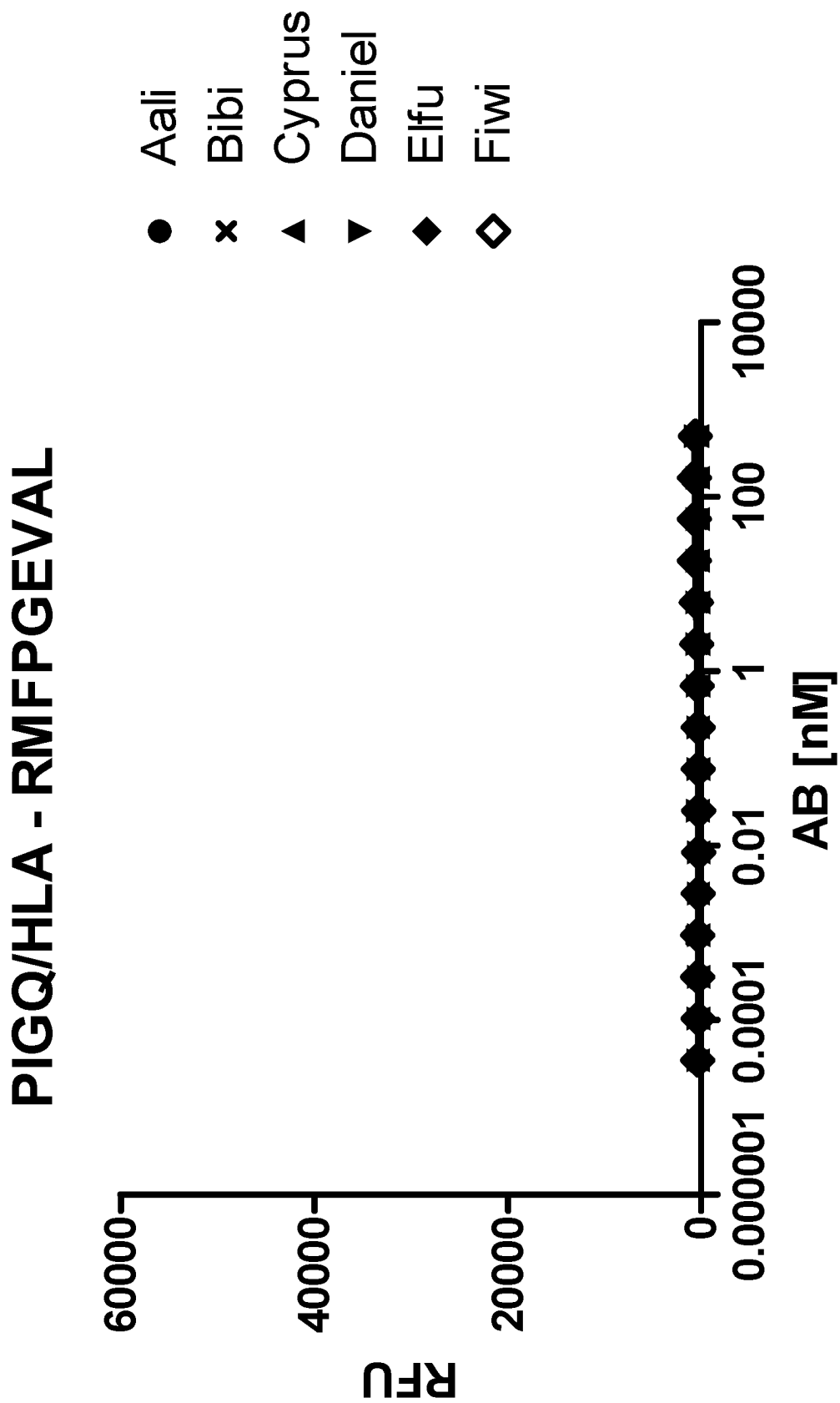
FIG. 6 shows the binding of the antibodies of the present disclosure to the PIGQ/HLA complex, i.e., an RMFPGEVAL (SEQ ID NO: 64)/HLA complex.

In this experiment the specificities of the antibodies of the present disclosure were investigated as described in Example 3. Results are shown in FIGS. 4-6.

It was found that all binders are highly specific for the RMF/HLA complex. None of the binders showed any cross-reactivity with either the RHAMM-HLA complex or the PIGQ/HLA complex. This is in striking contrast to the antibodies of the prior art (see Example 3), which all (with the exception of Refmab #18), showed cross-reactivity with a peptide/HLA-complex (PIGQ/HLA) that is expressed on healthy human tissue.

Example 8

Affinities and EC50's of the Binders in an Immunoglobulin Format

EC50 values were determined for the binders of the present disclosure and the binders of the prior art (ELISAs were performed on NEUTRAVIDIN plates). Results are summarized in Table 4. "++" designates binding with an EC50 of below 10 nM, "+" designates binding with an EC50 of more than 10 nM, and "---" designates no binding.

TABLE 4

Summary of EC50's of the binders (IgG) of the present invention

| Binder | EC50 on RMF/HLA [nM] | EC50 on RHAMM/HLA [nM] | EC50 on PIGQ/HLA [nM] |
|---|---|---|---|
| "Aali" | ++ | — | — |
| "Bibi" | ++ | — | — |
| "Cyprus" | ++ | — | — |
| "Daniel" | ++ | — | — |
| "Elfu" | ++ | — | — |
| "Fiwi" | ++ | — | — |
| Refmab #3 | ++ | — | + |
| Refmab #5 | ++ | + | + |
| Refmab #13 | ++ | — | ++ |
| Refmab #15 | ++ | — | ++ |
| Refmab #18 | ++ | — | — |
| Refmab #23 | ++ | + | + |

All binders (the binders of the present invention, as well as the binders of the prior art) showed very low EC50 values towards the RMF/HLA complex (with the exception of Refmab #3 and Refmab #5 all EC50's were in fact <1 nM). However, all binders of the prior art (except Refmab #18) also showed binding to the PIGQ/HLA counter antigens. Two binders of the prior art even showed binding to the RHAMM/HLA counter antigen.

The apparent affinity of the binders Aali and Refmab #13 was measured for the RMF/HLA antigen with an Octet system. The apparent affinity value for Refmab #13 was determined as 8.2 nM. The binding of Aali was characterized by a very slow dissociation rate, which exceeded the specification limits that were set in the system. Compared to Refmab #13 (8.2 nM), the apparent affinity of Aali is therefore <0.5 nM.

Example 9

Binding of the Antibodies of the Present Invention to Cells

Example 4 was repeated with the antibodies of the present disclosure, i.e. binding to RNF/HLA-positive SET2 cells (DSMZ No. ACC 608) and BV173 cells (DSMZ No. ACC 20) was tested by flow cytometry. EC50 values were determined. Results are shown in Table 5. "++" designates binding with an EC50 of below 10 nM, "+" designates binding with an EC50 of more than 10 nM, and "---" designates no binding to the target on cells.

TABLE 5

Summary of IgG characterization by flow cytometry

| Binder | EC50 on SET2 cells [nM] | EC50 on BV173 cells [nM] |
|---|---|---|
| "Aali" | ++ | + |
| "Bibi" | + | + |
| "Cyprus" | + | + |
| "Daniel" | ++ | + |
| "Elfu" | + | + |
| "Fiwi" | + | + |

All antibodies of the present invention show binding to WT1/HLA-expressing cells. This was also the case for most (4 out of 6) of the prior art antibodies, but most notably not for Refmab #18, the only reference antibody that does not bind to PIGQ/HLA.

The antibodies and binders of the present invention are therefore characterized in that they specifically bind to the RMF/HLA-complex without demonstrating any cross-reactivity to the PIGQ/HLA complex. In addition, the antibodies of the present disclosure also do bind to WT1/HLA expressing cell lines.

Example 7

Binding to Leukemic Patient Samples

The binders of the present invention are investigated for their ability to detect the RMF epitope on primary AML cells. The binders are expected to bind to AML blasts of patients. Results are confirmed by flow cytometry analysis. Results confirm that the level of RMF/HLA-A0201 on the surface of leukemia cells is adequate to allow for a reactivity with the binders of the present invention. The results also confirm that the levels of the target molecule on negative healthy cells are insignificant.

Example 8

Mediation of ADCC Activity

The binders of the present invention are also investigated for their potential to mediate ADCC, one of the major effector mechanisms of therapeutic antibodies in humans. In the presence of human PBMCs, the binders mediate a dose-dependent PBMC ADCC against T2 cells (an antigen-processing-deficient cell line, see, for example, WO 2012/135854) loaded with RMF peptide, but not T2 cells alone or T2 cells pulsed with a control peptide. The binders are also able to mediate ADCC against naturally presented RMF epitope by HLA-A0201 molecule on tumor cells, such as the mesothelioma cell line, JMN and the leukemia cell line BV173, but not to HLA-A2 negative cells, such as MSTO or HL-60. These results demonstrate that the binders mediates specific ADCC against cells that naturally express RMF and HLA-A0201 complex at physiologic levels as well as on cell lines.

Example 9

Elimination of Human Leukemia Cells in NSG Mice

The binders of the present invention are further investigated in an in vivo NOD SCID gamma (NSG) mice xenograft model. Mice are xenografted intravenously 6 days previously with BV173 bcr/abl positive acute lymphoblastic leukemia. At the time of treatment, mice developed leukemia in their liver, spleen, and BM as visible by luciferase imaging. The binders of the present invention dramatically reduce the tumor burden for at least 30 days. Results are confirmed by titrating the dose of the antibody.

---

What is claimed is:

1. An isolated antibody comprising an HCDR1 region consisting of SEQ ID NO: 7, an HCDR2 region consisting of SEQ ID NO: 8, an HCDR3 region consisting of SEQ ID NO: 9, an LCDR1 region consisting of SEQ ID NO: 10, an LCDR2 region consisting of SEQ ID NO: 11, and an LCDR3 region consisting of SEQ ID NO: 12, and wherein said antibody specifically binds to a complex of HLA-A0201/SEQ ID NO: 1.

2. The antibody of claim 1, wherein the antibody is in an Fab format.

3. The antibody of claim 2, wherein the antibody has an EC50 of less than 10 nM.

4. The antibody of claim 1, wherein the antibody is in an immunoglobulin format.

5. The antibody of claim 4, wherein the antibody has an EC50 of less than 10 nM.

6. The antibody of claim 1, wherein the antibody binds to the complex of HLA-A0201/SEQ ID NO: 1 with a dissociation rate of less than 0.5 nM.

7. The antibody of claim 1, wherein the antibody is humanized.

8. The antibody of claim 1, wherein said antibody binds to a complex of a peptide consisting of SEQ ID NO: 1 with HLA-A0201 with an EC50 that is at least 10 times lower than the EC50 for a complex of a peptide consisting of SEQ ID NO: 64 with HLA-A0201.

9. The antibody of claim 1, wherein said antibody does not bind a complex of a peptide consisting of SEQ ID NO: 64 with HLA-A0201.

10. The antibody of claim 1, wherein said antibody has an EC50 of less than 10 nM in a Fab format and in an immunoglobulin format.

11. The antibody of claim 1, wherein said antibody comprises a variable heavy chain comprising SEQ ID NO: 5 and a variable light chain comprising SEQ ID NO: 6.

12. A pharmaceutical composition comprising the antibody according to claim 1, and a pharmaceutically acceptable carrier and/or excipient.

13. An isolated antibody or an antigen-binding fragment thereof which specifically binds to a complex of HLA-A0201/SEQ ID NO: 1, wherein said antibody or antigen-binding fragment thereof comprises:
   (i) a heavy chain variable region (VH) comprising CDR regions HCDR1, HCDR2 and HCDR3 of SEQ ID NO: 5, and
   (ii) a light chain variable region (VL) comprising CDR regions LCDR1, LCDR2, and LCDR3 of SEQ ID NO: 6.

* * * * *